(12) United States Patent  (10) Patent No.: US 9,216,261 B2
Kaar et al.  (45) Date of Patent: Dec. 22, 2015

(54) DOSE COUNTER FOR A METERED-DOSE INHALER

(71) Applicant: IVAX INTERNATIONAL B.V., Utrecht (NL)

(72) Inventors: Simon G. Kaar, Cork (IE); Jeffrey A. Karg, Hopkinton, MA (US); Timothy Norman Johnson, Raymond, NH (US); Robert Charles Uschold, Leominster, MA (US)

(73) Assignee: IVAX International B.V., Utrecht (NL)

( * ) Notice: Subject to any disclaimer, the term of this patent is extended or adjusted under 35 U.S.C. 154(b) by 57 days.

(21) Appl. No.: 14/132,918

(22) Filed: Dec. 18, 2013

(65) Prior Publication Data

US 2014/0109904 A1   Apr. 24, 2014

Related U.S. Application Data

(63) Continuation of application No. 13/387,508, filed as application No. PCT/EP2010/004790 on Jul. 28, 2010, now Pat. No. 8,662,381.

(60) Provisional application No. 61/229,830, filed on Jul. 30, 2009.

(51) Int. Cl.
*A61M 11/00* (2006.01)
*G06M 1/06* (2006.01)
(Continued)

(52) U.S. Cl.
CPC ......... *A61M 15/009* (2013.01); *A61M 15/0076* (2014.02); *G06M 1/04* (2013.01); *G06M 1/083* (2013.01)

(58) Field of Classification Search
USPC ............................................. 235/87, 91, 103
See application file for complete search history.

(56) References Cited

U.S. PATENT DOCUMENTS 6,446,627 B1   9/2002 Bowman
7,819,075 B2   10/2010 Bowman et al.
(Continued)

FOREIGN PATENT DOCUMENTS

CN   1265601 A   9/2000
CN   1946448 A   4/2007
(Continued)

OTHER PUBLICATIONS

International Search Report, dated Nov. 4, 2010, International Appl. No. PCT/EP2010/004790, filed Jul. 28, 2010, IVAX Pharmaceuticals Ireland.
(Continued)

*Primary Examiner* — Daniel Hess
(74) *Attorney, Agent, or Firm* — RatnerPrestia

(57) ABSTRACT

A dose counter for counting doses of medicament dispensed by or remaining in a metered-dose inhaler. The dose counter includes: a rotatably mounted gear wheel having a circular arrangement of ratchet teeth; a display coupled to the gear wheel, the display having a visible array of dose counting indicia indexable in response to rotary motion of the gear wheel; and an actuator mechanism having a driver for rotatably driving the gear wheel in response to the dispensation of a medicament dose, the driver being arranged to engage the ratchet teeth of the gear wheel. The actuator mechanism includes a pivotally mounted lever having an input portion. The lever is arranged to amplify a linear stroke at the input portion such that a linear stroke of the driver exceeds the linear input stroke. By amplifying the stroke, the risk of undercounting due to insufficient stroke length may be reduced.

31 Claims, 26 Drawing Sheets

(51) Int. Cl.
*A61M 15/00* (2006.01)
*G06M 1/04* (2006.01)
*G06M 1/08* (2006.01)

(56) References Cited

U.S. PATENT DOCUMENTS

| | | |
|---|---|---|
| 7,832,351 B2 | 11/2010 | Bonney et al. |
| 2002/0047021 A1 | 4/2002 | Blacker et al. |
| 2003/0209239 A1 | 11/2003 | Rand et al. |
| 2007/0241025 A1 | 10/2007 | Parkes |
| 2008/0035144 A1 | 2/2008 | Bowman et al. |
| 2008/0156321 A1 | 7/2008 | Bowman et al. |
| 2010/0078490 A1 | 4/2010 | Fenlon |
| 2012/0247458 A1 | 10/2012 | Lawrence et al. |

FOREIGN PATENT DOCUMENTS

| | | |
|---|---|---|
| CN | 101198972 A | 6/2008 |
| GB | 2320489 A | 6/1998 |
| GB | 2348928 A | 10/2000 |
| JP | 2007-534378 | 11/2005 |
| WO | WO 92/09324 | 6/1992 |
| WO | WO 9828033 | 7/1998 |
| WO | 9856444 | 12/1998 |
| WO | WO 01/28887 A1 | 4/2001 |
| WO | WO 2005102430 A1 | 11/2005 |
| WO | WO 2006110080 A1 | 10/2006 |
| WO | WO 2008015542 | 2/2008 |
| WO | WO 2008119552 A1 | 10/2008 |
| WO | WO 2008121459 A1 | 10/2008 |

OTHER PUBLICATIONS

International Search Report, dated Oct. 29, 2010, International Appl. No. PCT/EP2010/004791, filed Jul. 28, 2010, IVAX Pharmaceuticals Ireland.

International Search Report, dated Nov. 9, 2010, International Appl. No. PCT/EP2010/004792, filed Jul. 28, 2010, IVAX Pharmaceuticals Ireland.

English translation of Chinese Office Action, dated Apr. 16, 2013, corresponding to counterpart application No. CN 201080041218.1.

English translation of Chinese Office Action, dated Apr. 15, 2013, corresponding to counterpart application No. CN 201080040988.4.

European Search Report, dated Feb. 7, 2014, corresponding to counterpart European Patent Application No. 13005367.1.

Entire patent prosecution history of U.S. Appl. No. 13/387,535, filed Jun. 8, 2012, entitled, "Dose Counter for a Metered-Dose Inhaler."

European Search Report dated Jan. 7, 2014 for European Patent Application No. 13004775.6.

Entire patent prosecution history of U.S. Appl. No. 13/387,508, filed Jun. 8, 2012, entitled, "Dose Counter for a Metered-Dose Inhaler," now U.S. Pat. No. 8,662,381, issued Mar. 4, 2014.

Entire patent prosecution history of U.S. Appl. No. 13/387,532, filed Jun. 8, 2012, entitled, "Dose Counter for a Metered-Dose Inhaler."

DOSE COUNTER FOR A METERED-DOSE INHALER

CROSS-REFERENCE TO RELATED APPLICATIONS

This application is a continuation patent application of U.S. patent application Ser. No. 13/387,508, filed Jun. 8, 2012, which is a U.S. National Phase patent application of International Patent Application No. PCT/EP2010/004790, filed Jul. 28, 2010, which claims priority to U.S. Provisional Patent Application No. 61/229,830, filed Jul. 30, 2009, each of which is incorporated by reference herein in its entirety.

FIELD OF THE INVENTION

This invention relates to a dose counter suitable for inclusion in a metered-dose inhaler. The invention also relates to a metered-dose inhaler which includes the dose counter and a method of counting doses dispensed from a metered-dose inhaler.

BACKGROUND OF THE INVENTION

Metered-dose inhalers include pressurised metered-dose inhalers (of both manually operable and breath-actuated types) and dry-powder inhalers. Such metered-dose inhalers typically comprise a medicament-containing vessel and an actuator body having a drug delivery outlet. The medicament-containing vessel may be a pressurised canister containing a mixture of active drug and propellant. Such canisters are usually formed from a deep-drawn aluminium cup having a crimped ferrule which carries a metering valve assembly. The metering valve assembly is provided with a protruding valve stem which, in use, is inserted as a tight push fit into a so-called "stem block" in the body.

To actuate the conventional manually operable inhaler, the user applies a compressive force to the closed end of the canister. The internal components of the metering valve assembly are spring loaded so that a compressive force of about 15 to 30 N is required to activate the device. In response to this compressive force, the canister moves axially with respect to the valve stem by an amount varying from about 2 to 4 mm. This degree of axial movement is sufficient to actuate the metering valve and cause a metered quantity of the drug and propellant to be expelled through the valve stem. This is then released into the mouthpiece via a nozzle in the stem block. A user inhaling through the drug delivery outlet of the device at this point will thus receive a dose of the drug.

Metered-dose inhalers as described above administer an accurate dose of medicament whenever required, which is particularly useful for users whose respiratory difficulties manifest themselves suddenly. Such has been the success of these devices that they are now used throughout the world.

A more recent development is the so-called breath-actuated metered-dose inhaler which delivers a dose of drug through a mouthpiece in response to inhalation by the user. This type of arrangement is particularly convenient in circumstances where the co-ordination between user inhalation and manual depression of the aerosol canister is imperfect. For example, children sometimes lack the necessary co-ordination to achieve effective self-administration and, at times of respiratory distress, adult users may also experience poor co-ordination.

One of the drawbacks of self-administration from an inhaler, whether manually operated or breath-actuated, is that users often experience difficulty in determining when the charge in the medicament-containing vessel has nearly run out, since the contents of the medicament reservoir are typically invisible to the user. With aerosol canisters, part of the reason for this difficulty is that a surplus of propellant may remain in the canister even though the drug supply is nearly exhausted. Alternatively, the near-exhausted state may result in a surplus of drug in relation to propellant. Thus, the illusion is created that the inhaler is still capable of providing useful doses of medicament simply because the canister contains liquid. This is potentially hazardous for the user since dosing becomes unreliable and because few users routinely carry a back-up device. Many users have several different inhalers for the treatment of a variety of conditions. Others keep inhalers at a number of different locations such as at school, home, work etc. In these circumstances it is particularly difficult for the user to keep track of the amount of usage extracted from each individual inhaler apparatus.

WO 98/28033 discloses a dose counter suitable for use with the above-described metered-dose inhalers. The dose counter enables users to assess how many doses remain in the obscured canister. Such a counter can provide a warning when the inhaler nears exhaustion so that appropriate measures can be taken to avoid running out of medication. Moreover, since the dose counter has a counting resolution of one dose, it can be used for compliance monitoring, either under hospital supervision or by parents and teachers assessing compliance by children in their care. Furthermore, there are regulatory requirements for metered-dose inhalers to have a dose counter in a number of countries.

FIGS. 1 to 3 reproduced herein from WO 98/28033 show the lower portion of a metered-dose inhaler. The inhaler comprises a body 2 having a drug delivery outlet 4. An aerosol canister 6 extends into the lower portion of the body 2. The aerosol canister 6 is formed from a deep-drawn aluminium cup 8 to which a ferrule 10 is attached by crimping.

The lid 10 carries a metering-valve assembly having a protruding valve stem 12, the end of which is received as a tight push fit in a stem block 14 of the body 2. Stem block 14 has a nozzle 16 communicating with the drug delivery outlet 4 so that, upon actuation of the metering-valve assembly, a charge of the drug is emitted through the nozzle 16 into the drug delivery outlet 4. Actuation of the metering-valve assembly is effected by causing downward movement of the aerosol canister 6 relative to the body 2. This may be achieved through manual pressure exerted by the user against the upturned base (not shown) of the aerosol canister 6 or by automatic depression of the aerosol canister 6 in response to user inhalation in inhalers of the breath-actuated type. The mechanism of actuation does not form part of WO 98/28033 or the present invention and will not be described in further detail. A user inhaling through the drug delivery outlet 4 when the aerosol canister 6 is depressed will receive a metered dose of the drug.

With reference to the Figures, a counter mechanism 18 includes an actuator shaft 20 moulded from a plastics material, such as nylon, the actuator shaft 20 having a boss 22 integrally formed at its base. The underside of boss 22 is formed with a blind hole which receives a compression spring 24 mounted on an upstanding spigot 26 formed on a lower element of the counter chassis.

A driver 28 for driving a rotary gear in the form of a ratchet-toothed wheel 30 is integrally moulded with boss 22 of the actuator shaft 20 and comprises a transverse hook element mounted between two arms (only one of which is visible in FIG. 2), the bases of which are conjoined to the boss 22. The transverse hook is dimensioned and oriented to engage with ratchet teeth 32 formed around the periphery of the ratchet-toothed wheel 30 to rotate it in a forward direction.

The ratchet-toothed wheel 30 is integrally moulded with a first hollow axle 34 which is rotatably supported on a first spindle 36 that projects transversely from a chassis sub-element 38. Chassis sub-element 38 also has a second spindle 40 projecting transversely therefrom on which a second hollow axle 42 is rotatably supported. A flexible tape 44 is wound around the second hollow axle 42 which serves as a supply spool and passes to the first hollow axle 34 which serves as a take-up spool (stock bobbin). A guide plate 46 forming part of the chassis sub-element 38 helps to guide the tape 44 in a smooth passage from the supply spool to the take-up spool. The surface of the tape 44 is marked with a progression of descending numbers which denote the number of doses remaining in the aerosol canister. Typically, the starting count is 200 and successive markings on the tape decrease by one. The spacing between successive markings is coincident with the indexing motion of the ratchet-toothed wheel 30 so that a new number appears in a window 48 provided in the body 2 for each successive actuation.

The ratchet-toothed wheel 30 and integrally formed first hollow axle 34 are restrained from reverse rotation by a wrap-spring clutch 50 surrounding the hollow axle 34 at the end thereof remote from ratchet-toothed wheel 30. One end (not shown) of the wrap-spring clutch 50 is braced against the counter chassis. The windings of the wrap-spring clutch 50 are oriented such that rotation of the first hollow axle 34 in a forward sense is not resisted by the spring coils. However, reverse rotation of the hollow axle 34 acts so as to tighten the spring coils around it, thereby causing the first hollow axle 34 to be gripped by the internal surface of the wrap-spring clutch 50 and hence restraint from reverse rotation.

FIG. 3 shows a more detailed view of the principal elements of the dose counter 18. It will be seen that the driver 28 comprises the transverse hook 52 mounted between a pair of arms 54, 56 which are joined at their bases by a web. The web is connected to the boss 22 of the actuator shaft 20. A combined actuator and driver assembly may be integrally formed, such as from a plastics material, e.g. as nylon.

In use of the dose counter 18, depression of the canister 6 causes the ferrule 10 to engage with the actuator shaft 20, which actuator shaft 20 moves downwards against the compression spring 24. The transverse hook 52, in turn, engages with the ratchet teeth 32 of the ratchet-toothed wheel 30 which is mounted on the hollow axle 34 serving as the take-up spool for the flexible tape display 44. At the end of the hollow axle 34 remote from the ratchet-toothed wheel 30 is the clutch 50 which serves to restrain the axle 34 against reverse rotation and hence prevents reverse travel of the counter tape 44.

A control surface 58 is depicted in FIG. 3 as a see-through element so that the workings of the dose counter may be more clearly seen. The control surface 58 extends parallel to the direction of travel of the actuator shaft 20 and is located adjacent the ratchet-toothed wheel 30 at a position which marks a chordal projection across one of the wheel faces. One of the support arms 56 of the driver 28 is in sliding contact with control surface 58. This sliding contact serves to inhibit the natural tendency of the driver 28 to flex radially inwardly towards the axis of rotation of the ratchet-toothed wheel 30. By preventing such radially inward flexure, the control surface 58 restricts the engagement and disengagement of the drive 28 with the ratchet-toothed wheel 30 so that the distance by which the ratchet-toothed wheel 30 rotates is limited to one tooth pitch. This condition is observed regardless of the extent of linear travel, or stroke, of the actuator shaft 20.

FIG. 4 shows a schematic view of an alternative arrangement for the ratchet-toothed wheel and driver used in the dose counter 18 described in WO 98/28033. The alternative arrangement uses a reciprocating driver 28 acting in a pushing sense to rotate a ratchet-toothed wheel 30 in the direction shown by the arrows 31. A fixed pawl 60 acts to prevent reverse rotation of the ratchet-toothed wheel 30 by engagement against the trailing edge 62 of a ratchet tooth 32. However, on forward rotation of the ratchet-toothed wheel 30 in the sense of arrows 31, the fixed pawl 60 is capable of radially outward deformation, urged by the leading edge 63 of a ratchet-tooth 32.

In this arrangement, if the ratchet-toothed wheel 30 is rotated by more than a single tooth pitch but by less than two tooth pitches for each reciprocating movement of the driver 28, there is a degree of reverse rotation until the pawl 60 becomes engaged by the trailing edge 62 (as opposed to the leading edge 63) of a ratchet tooth 32. Thus, the rotation of the ratchet-toothed wheel 30 may be described as "stepped".

The components of metered-dose inhalers are manufactured to a high technical specification. However, inevitable variations in the tolerances of the components can, in some circumstances, lead to failure of the dose counter of the type disclosed in WO 98/28033. In a known failure mode, the reciprocating stroke of the canister is insufficient to fully increment the dose counter. This may lead to undercounting, particularly where rotation of the ratchet-toothed wheel is stepped, as illustrated in FIG. 4.

Another problem relates particularly to manually operated metered-dose inhalers. In these types of inhaler, the user cannot be relied upon to repeatably actuate the inhaler with a full reciprocating stroke of the canister. Instead, the user may on some occasions release the canister immediately after the "fire point" of the metering valve, that is to say the point in the stroke at which the medicament is dispensed. This reduced stroke of the canister available for incrementing the dose counter may exacerbate the problem described above.

Overtravel, or excessive travel, of the canister can also cause problems in relation to dose counters.

There is a requirement in the art, therefore, for a dose counter with a reduced failure rate. There is a particular requirement for such a dose counter which can be manufactured efficiently and incorporated into known metered-dose inhalers, and which can accommodate overtravel of the canister.

SUMMARY OF THE INVENTION

According to a first aspect of the present invention, there is provided a dose counter for counting doses of medicament dispensed by or remaining in a metered-dose inhaler, the dose counter comprising:

a rotatably mounted gear wheel having a circular arrangement of ratchet teeth;

a display coupled to the gear wheel, the display having a visible array of dose counting indicia indexable in response to rotary motion of the gear wheel; and an actuator mechanism having a driver for rotatably driving the gear wheel in response to the dispensation of a medicament dose, the driver being arranged to engage the ratchet teeth of the gear wheel, wherein the actuator mechanism comprises a pivotally mounted lever or linkage having an input portion, the lever or linkage being arranged to amplify a linear stroke at the input portion such that a linear stroke of the driver exceeds the linear input stroke.

The counter of the present invention thus provides an actuator mechanism which is able to amplify the stroke of a linear input means such as the ferrule of a medicament canister. That is to say, the linear travel of the driver is greater than the linear travel at the input portion of the lever.

The increased stroke of the driver may provide sufficient travel for the dose counter to be reliably incremented, even when the medicament canister is released by the user immediately after the fire point, and even when there is a large degree of accumulated variation, or tolerance stack, in the components of the inhaler. Miscounting or non-counting of doses can thereby be avoided, which in turn significantly reduces the failure rate of the dose counter. Dose counters of the type disclosed in WO 98/28033 have been found to be particularly suitable for modification according to the principles of the present invention.

In operating the dose counter, a small increase in actuating force will be required compared to dose counters of the type disclosed in WO 98/28033. For a metered-dose inhaler comprising a pressurised medicament canister, this increase in actuating force generally remains insignificant compared to the force required to overcome the internal valve spring of the canister.

Herein, the term "linear stroke" generally refers to the straight line distance covered at the input portion of the lever arm, or the input portion of the linkage, or the driver, from the start of the stroke to the end of the stroke. In practice, these elements may follow an arcuate path, the radius of which will depend on the particular geometry of the dose counter.

The lever or linkage may be arranged such that the linear stroke of the driver is at least 1.1 times, preferably at least 1.15 times, and most preferably at least 1.2 times, the linear input stroke. In this way, a significant amplification of the input stroke is achieved.

In some embodiments of the dose counter, the actuator mechanism comprises the pivotally mounted lever, with the pivotal mounting being arranged between the input portion and an output portion of the lever. The input portion of the lever may be arranged at an end of the lever.

In other embodiments of the dose counter, the actuator mechanism still comprises a pivotally mounted lever, but the input portion of the lever is arranged between the pivotal mounting and an output portion of the lever. These embodiments may be advantageous in that the travel of the input portion and the travel of the output portion may be in the same direction. In embodiments of this type the input portion of the lever may be defined by a projection extending from the lever in a direction substantially perpendicular to an imaginary line joining the pivotal mounting and the output portion. Alternatively, the input portion may be defined by a bend in the lever.

A variety of configurations for the actuator mechanism are suitable. For example, the actuator mechanism may be configured so that a medicament canister arranged for reciprocating movement contacts the input portion of the lever directly or via a separate actuator shaft arranged for reciprocating movement. The output portion of the lever may itself carry the driver which engages the gear wheel ratchet teeth, or the driver may be carried by a separate driver shaft arranged for reciprocating movement and for engagement by the output portion of the lever.

In embodiments including a separate actuator shaft for contact by the medicament canister, the actuator shaft is mounted for reciprocating movement and an output portion of the actuator shaft is arranged to engage the input portion of the lever. The actuator shaft may be resiliently biased towards a starting position, the actuator shaft being displaceable against the resilient bias to engage the input portion of the lever. In a particular embodiment, the actuator shaft and lever are arranged such that, in use of the dose counter, pivotal movement of the lever causes the output portion of the actuator shaft to slide across and become misaligned with the input portion of the lever, such that the actuator shaft may continue to move linearly after the pivoting lever (and driver) has reached the end of its travel. In this way, the mechanism may accommodate overtravel, or excessive travel, of the medicament canister.

In embodiments in which the output portion of the lever caries the driver, the lever may be resiliently biased towards a starting position, the lever being displaceable against the resilient bias in response to the linear input stroke. The resilient bias may be provided by at least one of: a leaf spring separate from the lever, a leaf spring integrally formed with the lever, and a compression spring and a torsion spring.

In embodiments including a separate driver shaft which carries the driver, the driver shaft is arranged for contact by the output portion of the lever and is mounted for reciprocating movement. The driver shaft may be resiliently biased towards a starting position, the driver shaft being displaceable against the resilient bias in response to engagement by the output portion of the lever. The resilient bias may, for example, be provided by a compression spring.

In some embodiments, the lever is arranged such that the direction of movement of the output portion is substantially perpendicular to the direction of movement of the input portion. In other embodiments, the lever is arranged such that the direction of movement of the output portion is substantially parallel to the direction of movement of the input portion.

A variety of different types of pivotal mounting are suitable for the lever. For example, the lever may be rotatably mounted to a separate mounting structure to thereby provide the pivotal mounting. The rotatable mounting may comprise a male member formed on one of the lever and the mounting structure and received in a hole or opening formed in the other of the lever and the mounting structure.

Alternatively, a mounting end of the lever may be provided with a tongue which is narrower than the lever, and the tongue may be inserted through an aperture or slot formed in a thin walled mounting structure. The end of the lever having the tongue is then able to rotate about the aperture or slot, to thereby provide the pivotal mounting of the lever. In another arrangement a mounting end of the lever is simply received in a channel formed in a mounting structure, which arrangement allows limited pivotal movement of the lever.

The pivotal mounting of the lever may also be provided as one of a variety of different types of flexure hinges. In this case, the lever may be integrally formed with a mounting structure, the flexure hinge being located between the lever and the mounting structure. For example, the lever and mounting structure may be defined by a moulded plastics component, in which case the flexure hinge is a living hinge. The lever and mounting structure may alternatively be defined by a stamped metal component, preferably a thin-walled component, in which case the flexure hinge may be a portion of the component having reduced flexural strength such that, in use of the dose counter, deformation at the flexure hinge is substantially elastic. The stamped metal component may have a cantilever configuration.

When the pivotal mounting is provided as a flexure hinge, the integrally formed mounting structure may be provided with an aperture or slot for receiving a male locating feature of a housing component of the dose counter or inhaler. The mounting structure may define at least one barb-like feature adjacent to the aperture or slot for engagement with the male locating feature. The barb-like feature may serve to attach the mounting structure to the housing component.

The lever may be provided with a second flexure hinge for accommodating overtravel at the input portion. The second flexure hinge may be arranged between the pivotal mounting and the output portion of the lever, the flexure hinge comprising a portion of the lever having reduced flexural strength. In use of the dose counter, the second flexure hinge is elastically deformable to allow continued travel at the input portion after the output portion (and driver) has reached the end of its normal travel.

Alternatively, overtravel at the input portion of the lever may be accommodated by configuring the pivotal mounting to be linearly displaceable against a resilient bias, such as a compression spring. In this way, the input portion of the lever may be allowed to continue to move after the output portion (and the driver) has reached the end of its travel. The resilient bias may have a preload so that the pivotal mounting only displaces after the dose counter has been actuated.

In a specific embodiment of the dose counter, the lever is provided with a through-hole or opening having an axis extending in a direction perpendicular to the pivotal axis, and in a direction substantially parallel to the direction of travel at the input portion of the lever. A fixed mounting post with a flanged head (preferably T-shaped) extends through the through-hole or opening with a clearance fit sufficient to provide the pivotal mounting. The mounting post also carries a preloaded compression coil spring which urges the lever against the flanged head of the post. The lever is displaceable along the post, against the compression spring, to allow the input portion of the lever to continue to move after the output portion has reached the end of its travel. The spring preload exceeds the force required at the input portion of the lever to actuate the dose counter, so that the pivotal mounting is not displaced linearly until after the dose counter has been actuated.

The dose counter may be provided with means to prevent reverse rotation of the gear wheel, such as a pawl arranged to engage the ratchet teeth of the gear wheel. This means may provide step-wise rotation of the gear wheel.

The driver may be arranged to rotatably drive the gear wheel on a forward or a return stroke. The driver may also be arranged such that its engagement surface extends in a direction parallel to the axis of the gear wheel (and its ratchet teeth) at substantially the middle of its normal stroke. In this way, the angles at which the driver engages the ratchet teeth of the gear wheel can be minimised, thereby minimising component wear. A control surface may be provided to regulate the position of engagement and disengagement between the driver and the gear wheel.

The display may comprise a flexible tape arranged between an indexing spool and a stock bobbin. The dose counting indicia of the display may include a unique indicium for display after each and every dose has been dispensed. The dose counting indicia may comprise at least 50 unique dose counting indicia representative of a number of doses dispensed by or remaining in the inhaler.

According to a second aspect of the present invention, there is provided a metered-dose inhaler comprising a medicament canister, an actuator body for receiving the canister and having a medicament delivery outlet, and the dose counter described above.

According to a third aspect of the invention, there is provided a method of counting doses dispensed from a metered-dose inhaler, the dose counter comprising:

a rotatably mounted gear wheel having a circular arrangement of ratchet teeth;

a display coupled to the gear wheel, the display having a visible array of dose counting indicia indexable in response to rotary motion of the gear wheel; and an actuator mechanism comprising a pivotally mounted lever or linkage having an input portion and further comprising a driver for rotatably driving the gear wheel in response to the dispensation of a medicament dose, the driver being arranged to engage the ratchet teeth of the gear wheel, the method comprising depressing a medicament canister to engage the input portion of the lever or linkage, to thereby cause the driver to rotatably drive the gear wheel, wherein a linear input stroke at the input portion of the lever or linkage is amplified such that a linear stroke of the driver exceeds the linear input stroke.

The third aspect of the invention corresponds to use of the dose counter or metered-dose inhaler described above. As such, the method may include using any of the features of the dose counter described above.

BRIEF DESCRIPTION OF THE DRAWINGS

The present invention will now be described, by way of example only, with reference to the accompanying drawings, in which.

DETAILED DESCRIPTION

Dose counters of the present invention are based on that shown in FIGS. 1 to 4 described hereinabove, except that the actuator mechanism is modified by varying degrees. Thus, the invention generally provides a dose counter comprising a rotatably mounted gear wheel having a circular arrangement of ratchet teeth and a display coupled to the gear wheel. The display has a visible array of dose counting indicia indexable in response to rotary motion of the gear wheel. The dose counter also comprises an actuator mechanism having a driver for rotatably driving the gear wheel in response to the dispensation of a medicament dose, the driver being arranged to engage the ratchet teeth of the gear wheel. According to the invention, the actuator mechanism comprises a pivotally mounted lever or linkage having an input portion. The lever or linkage is arranged to amplify a linear stroke at the input portion such that a linear stroke of the driver exceeds the linear input stroke.

Figure 5:
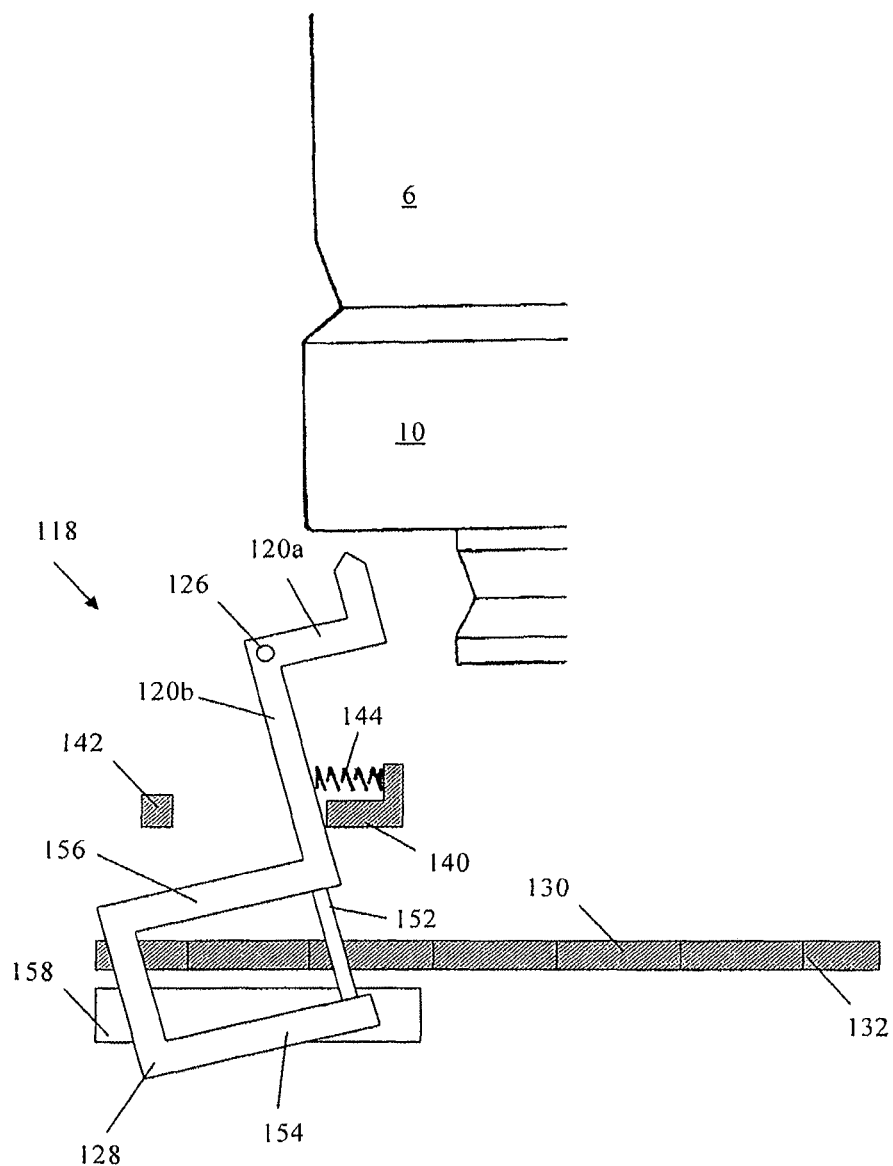
FIG. 5 is a schematic view of a first dose counter according to the present invention.
Figure 6:
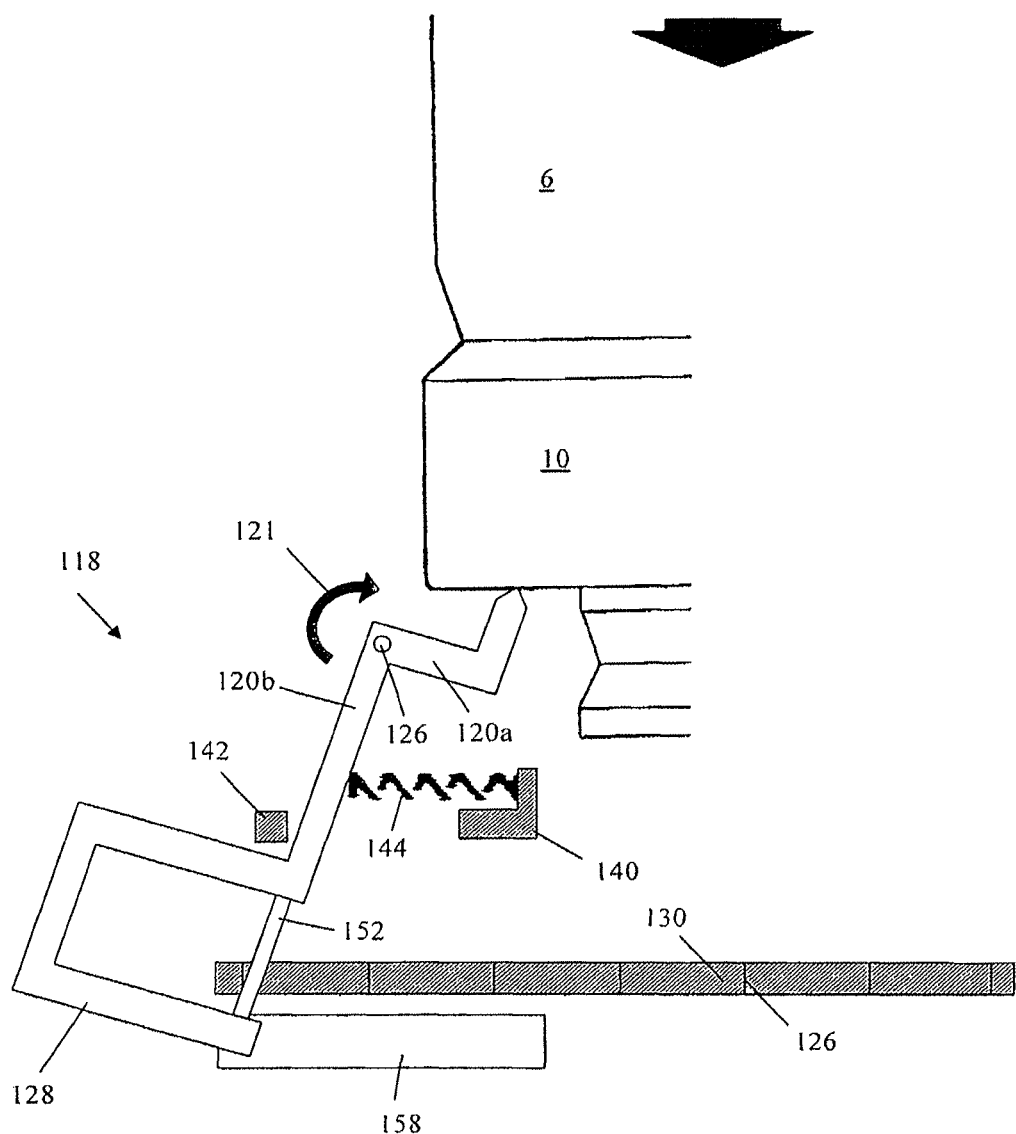
FIG. 6 is a schematic view similar to that of FIG. 5 for use in explaining the operation of the first dose counter.

A first dose counter according to the present invention will now be described with reference to FIGS. 5 to 9c. The actuator mechanism 118 of the first dose counter is shown schematically in FIG. 5, together with the gear wheel in the form of a ratchet-toothed wheel 130. The dose counter display (not shown in FIG. 5) is essentially the same as that illustrated in FIGS. 1 to 3, except that it is rotated 90 degrees so that it can be coupled to the ratchet-toothed wheel 130 without further modification. FIG. 6 also shows part of a pressurised medicament container 6 with which the first dose counter may be used.

The ratchet-toothed wheel 130 has essentially the same configuration as that of the wheel 30 illustrated in FIGS. 1 to 4. Thus, a plurality of ratchet teeth 132 are arranged about a circular periphery of the wheel 130. The ratchet-toothed wheel 130 is integrally moulded with a hollow axle (not shown) serving as an indexing spool of the display. The hollow axle is rotatably supported on a spindle that projects from the chassis of the first dose counter.

Figure 1:
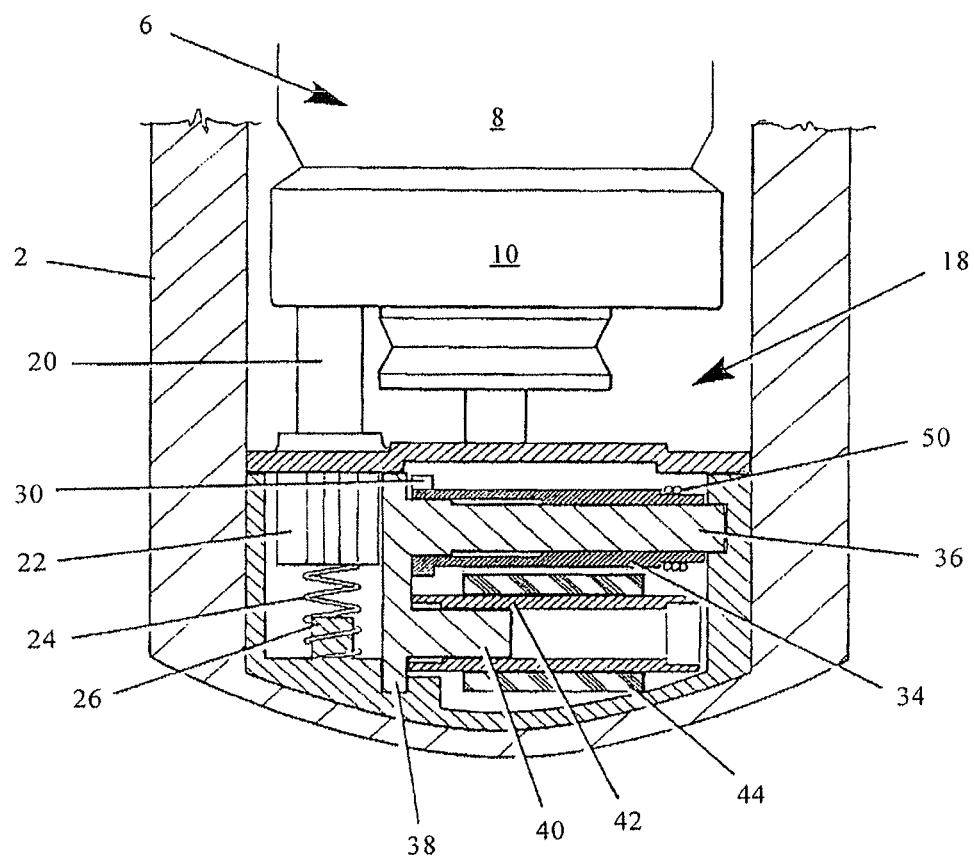
FIGS. 1 to 4 are views of a dose counter for a metered-dose inhaler according to the prior art document WO 98/28033.
Figure 2:
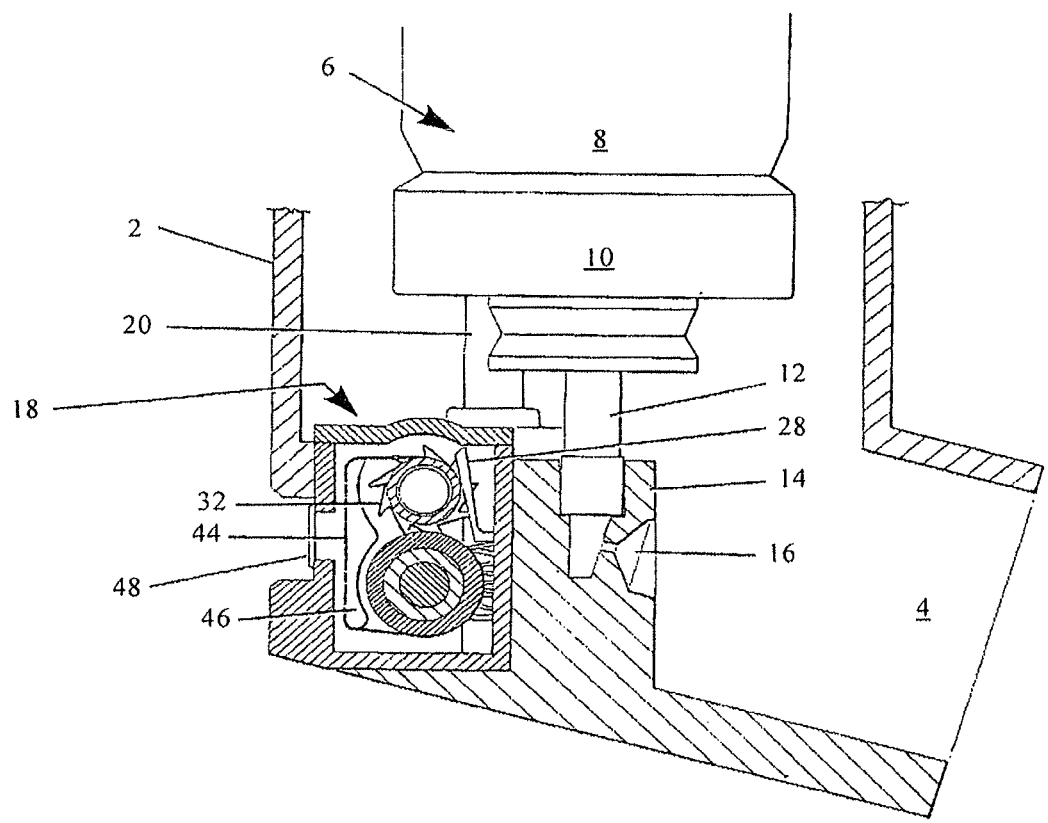
Figure 3:
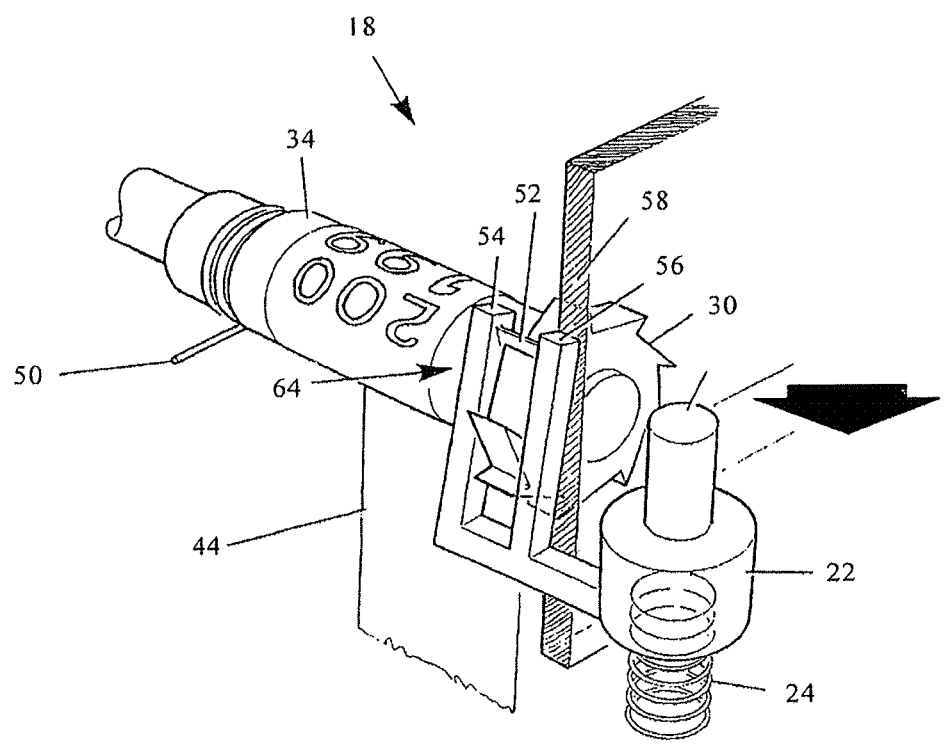
Figure 4:
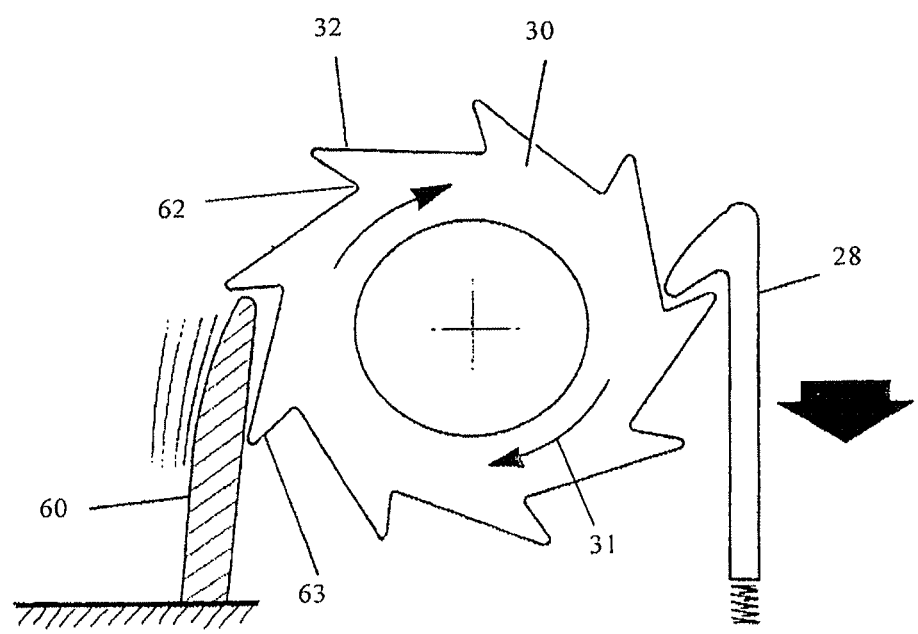

The ratchet-toothed wheel 130 is restrained from reverse rotation by a fixed pawl (not shown in FIG. 5) of the type illustrated in FIG. 4. The fixed pawl also provides step-wise rotation of the ratchet-toothed wheel since, if the wheel 130 is rotated by more than a single tooth pitch but by less than two tooth pitches, there is a degree of reverse rotation until the pawl becomes engaged by the trailing edge of a ratchet tooth 132.

The actuator mechanism 118 of the first dose counter differs from the actuator mechanism shown in FIGS. 1 to 4 in that, instead of comprising an actuator shaft mounted for reciprocation linear (translational) movement, it comprises a pivotally mounted member 120 arranged for rotational movement about an axis 126 that is perpendicular to the axis of the medicament canister 6.

The member 120 takes the form of a lever arm having a pair of rigidly connected limbs 120a, 120b extending from the pivotal mounting 126, to thereby define a right angle.

A first one of the limbs 120a is an input limb for engagement by the medicament canister 6 and extends in a generally transverse direction. The first limb is "L" shaped (right angled), with a distal end of the limb 120a extending in the same direction as, and away from, the other limb 120b. The first limb 120a has a length A (see FIG. 8) from the pivotal mounting 126 to the right angled bend of the "L" shape. The distal end of the first limb 120a is tapered so that a contact area engaged by the medicament canister 6 during linear movement of the canister 6 is minimised.

A second one of the limbs 120b is an output limb for driving rotational movement of the ratchet-toothed wheel 130 and extends in a generally downwards direction. The second limb 120b is provided at its distal end with a driver 128. The driver 128 comprises an elongated ratchet drive pawl 152 which extends in a direction parallel to the second limb 120b and is supported between a pair of perpendicular arms 154, 156, one of which is conjoined to the second limb 120b. The second limb 120b has a length B (see FIG. 8), which is greater than length A, from the pivotal mounting 126 to the mid-point of the ratchet drive pawl 152.

As in the dose counter 18 of WO 98/28033, the first dose counter 118 of the present invention further comprises a control surface 158 to accurately regulate the position of engagement and disengagement between the driver 118 and the ratchet-toothed wheel 130.

The rotational movement of the member 120 is limited by first and second detents 140, 142 integrally moulded into the chassis of the dose counter (not shown). The detents 140, 142 are arranged on transversely opposite sides of the second limb 120b in the vicinity of the driver 128. The second limb 120b is biased into contact with the first detent 140 by a tension spring 144 arranged therebetween. The second limb 120b is biased into a starting position which defines a slight acute angle with the axis of the ratchet-toothed wheel 130 for reasons which will become clear from the following description. The second detent 142 limits maximum movement of the second limb 120b away from the starting position and may be omitted in some embodiments. The second detent must allow sufficient movement of the second limb 120b to ensure that the valve of the medicament canister 6 can be fired with allowances for tolerance stack and lost motion.

Use of the first dose counter 118 for counting doses dispensed from a metered-dose inhaler will now be described with reference to FIG. 6. FIG. 6 is a schematic view showing the same components that are illustrated in FIG. 5. The other components of the metered-dose inhaler and the first dose counter 118 are omitted for clarity.

The metered-dose inhaler is actuated by the user applying a manual compressive force to the closed end of the canister 6. In response to this compressive force, the canister 6 moves axially with respect to its valve stem (not shown) by an amount varying from about 2 to 4 mm. Approximately 2 mm of displacement is required to fire the valve and dispense a dose of medicament. After the medicament has been dispensed, the user releases the compressive force and the canister 6 returns to its starting position under the action of the internal valve spring. The first dose counter 118 is driven by the reciprocating linear movement of the canister 6.

The downwards movement of the canister 6 causes the ferrule 10 of the canister 6 to engage with and displace the distal (input) end of the first limb 120a of the actuator member 120. The displacement causes the member 120, including the second limb 120b, to rotate in a clockwise direction against the bias of the tension spring 144, as indicated by arrow 121 in FIG. 6. The distal end of the first limb 120a slides across the face of the ferrule 10 as the member 120 rotates.

The ratchet drive pawl 152 of the driver 128 is dimensioned and orientated to engage with the ratchet teeth 132 of the ratchet-toothed wheel 130. The start and end positions of the actuator member 120, as shown in FIGS. 5 and 6 respectively, are arranged such that the ratchet drive pawl 152 extends in a direction parallel to the axis of the ratchet-toothed wheel 130 (and its teeth) midway through its normal stroke. In this way, an angle between the ratchet drive pawl 152 and the teeth 132 of the ratchet-toothed wheel 130 can be minimised, thereby reducing component wear.

Figure 7:
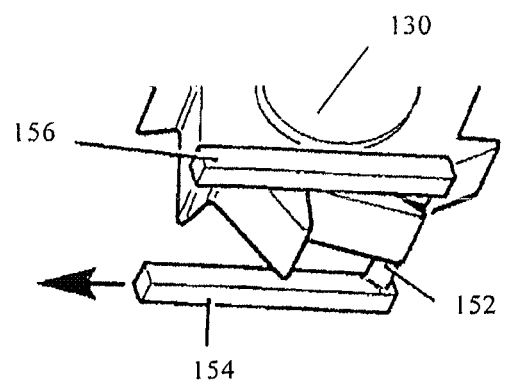
FIG. 7 is a perspective view of elements of the first dose counter shown in greater detail.

The engagement of the ratchet teeth 132 by the ratchet drive pawl 152 described hereinabove is illustrated more clearly in FIG. 7. Other elements of the first dose counter 118, including the second limb 120b of the actuator 120 to which the driver 128 is conjoined, are omitted from the Figure for clarity.

The ratchet drive pawl 152 rotates the ratchet-toothed wheel 130 by slightly more than a single tooth pitch. As described hereinabove, the control surface 158 serves to accurately determine the points of engagement and disengagement of the ratchet drive pawl 152 with the ratchet teeth 132 of the ratchet-toothed wheel 130. Following the disengagement, there is a small degree of reverse rotation of the ratchet-toothed wheel 130 until the fixed pawl (not shown) abuts the trailing edge of one of the ratchet teeth 132 of the ratchet-toothed wheel 130, at which point the wheel 130 (and thus the display) is indexed by exactly one tooth pitch.

Figure 8:
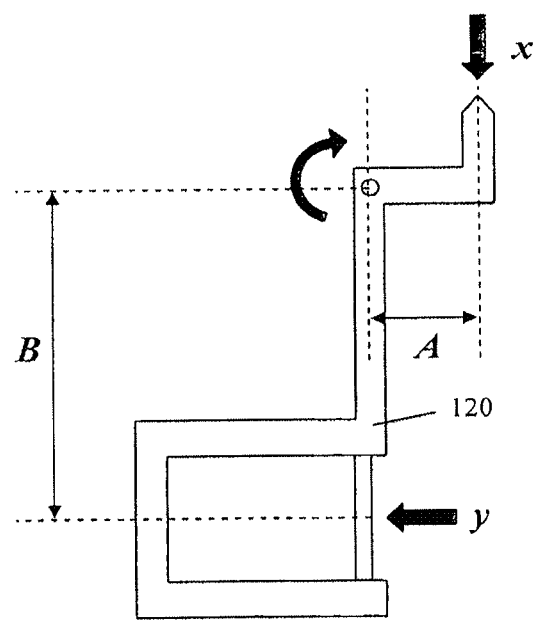
FIG. 8 is a view of an element of the first dose counter for further use in explaining its operation.

The actuator member 120 is schematically shown in isolation in FIG. 8. The relationship between the linear strokes of the distal (input) end of the first limb 120a and the driver 128 conjoined to the second limb 120b can be approximated by the following equation:

$$y = \frac{B}{A}x \quad (1)$$

where x and y are the linear strokes of the input end and the driver and A and B are the lengths indicated in FIG. 8 and described above. Since B is greater than A, the actuator member 120 serves to amplify the linear input stroke, providing the driver with increased travel.

By amplifying the linear input stroke, the length of the stroke available for indexing the ratchet-toothed wheel 130 is increased as compared to the dose counter of the type shown in FIGS. 1 to 4. This reduces the risk of miscounting, particularly undercounting and, in turn, reduces the failure rate of the dose counter.

The amplification of the linear input stroke is particularly advantageous for manually operated metered-dose inhalers, since the linear input stroke with this type of inhaler may be as small as 1.5 mm when the medicament canister 6 is released immediately after the fire point of the valve has been reached.

The amplification of the linear input stroke can also reduce the risk of miscounting due to accumulated tolerance stacks and lost motion, as will be explained with reference to FIGS. 9a to 9c.

Figures 9A, 9B, 9C:
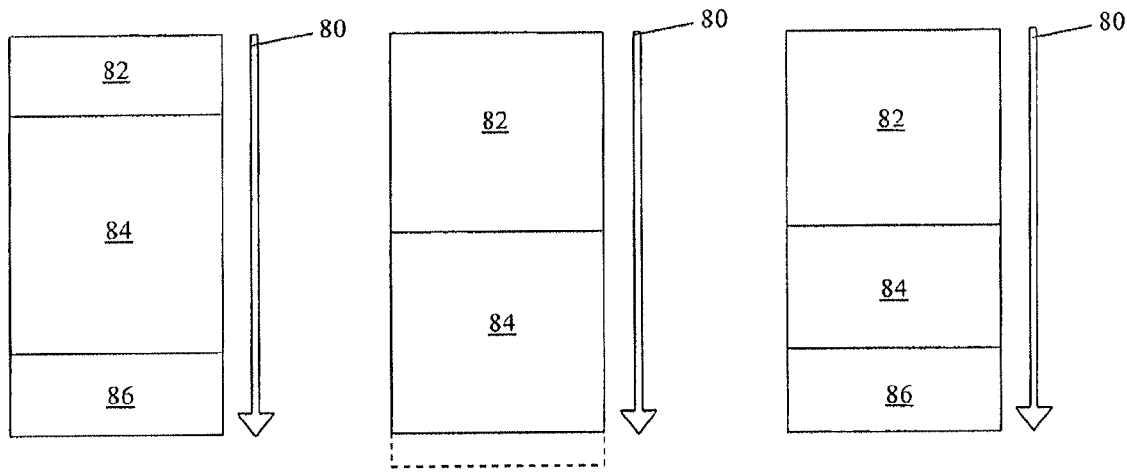
FIGS. 9a to 9c are graphical representations of the medicament canister travel during actuation of three metered-dose inhalers.

FIG. 9a is a graphical representation of the travel 80 of the medicament canister of a first inhaler having a working dose counter of the type shown in FIGS. 1 to 4. A first portion of the travel 82 takes up the accumulated tolerances of the manufactured components and any lost motion. A second portion of the travel 84 is the travel required to increment the dose counter. A third portion of the travel 86 is "excess" travel which would have been available had the accumulated tolerances or lost motion been greater.

FIG. 9b is a graphical representation of the travel 80 of the medicament canister of a second inhaler having a non-working (failed) dose counter of the type shown in FIGS. 1 to 4. The total canister travel 80 is the same as that for the first inhaler shown in FIG. 9a. Again, a first portion of the travel 82 takes up the accumulated tolerances of the manufactured components and any lost motion. The accumulated tolerances and lost motion are significantly greater in the second inhaler than they were in the first inhaler, so that the first portion of the travel 82 is correspondingly greater. A second portion of the travel 84 is the travel required to increment the dose counter, and this is the same as that shown in FIG. 9a for the first inhaler. However, there is insufficient remaining canister travel 80 to increment the dose counter, which causes the dose counter to fail.

FIG. 9c is a graphical representation of the travel 80 of the medicament canister of a third inhaler having the first dose counter according to the invention shown in FIG. 5. The total canister travel 80 is the same as that for the first and second inhalers shown in FIGS. 9a and 9b. Again, a first portion of the travel 82 takes up the accumulated tolerances of the manufactured components and any lost motion. The accumulated tolerances and lost motion are the same as those of the second inhaler which led to failure of the second inhaler's dose counter. A second portion of the travel 84 is the travel required to increment the dose counter. This second portion of the travel 84 is significantly less than it is for the first and second inhalers shown in FIGS. 9a and 9b, since the second portion of the travel 84 is amplified by the dose counter. Consequently, there is sufficient remaining canister travel 80 to increment the dose counter and the dose counter does not fail. A third portion of the travel 86 is the "excess" travel which would have been available had the accumulated tolerances or lost motion been even greater.

Thus, it will be seen that amplification of the linear input stroke can lead to a reduction in failures caused by excessive accumulated tolerances and lost motion. Amplification of the linear input stroke according to the principles of the present invention may lead to a small increase in the force with which the medicament canister 6 must be depressed. The force required for operating the dose counter 118, however, generally remains small compared to the force that is required to overcome the canister's internal valve spring.

Figure 10:
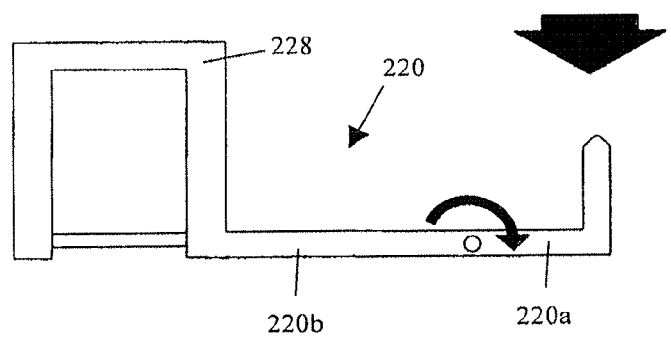
FIG. 10 is a view of a variation to the element shown in FIG. 8 for use in a second dose counter according to the present invention.

FIG. 10 shows an alternative actuator member design for use in a second dose counter according to the present invention. The modified actuator member 220 differs from the actuator 120 shown in FIG. 5 in that, instead of defining a right angle, the first and second limbs 220a, 220b are arranged in a straight line. With this arrangement, the distal (input) end of the first limb 220a and the driver 228 conjoined to the second limb 220b move in directions which are substantially parallel (but opposite) to each other. Thus it will be appreciated that the principle of using a pivotally mounted actuator 120, 220 provides a large degree of flexibility in the positioning and orientation of components.

A third dose counter 318 according to the present invention will now be described with reference to FIGS. 11 to 14. The third dose counter 318 is closely based on the dose counter 18 shown in FIGS. 1 and 2. Thus, the third dose counter 318 includes all of the components of the counter shown in FIGS. 1 and 2, including the actuator shaft 20 which serves to actuate the dose counter 318, the ratchet-toothed wheel 30, the spindles 36, 40 and the flexible tape 44. A detailed description of these components of the third dose counter 318 will therefore be omitted, except to the extent that their form or function differs from that described hereinabove.

Figure 11:
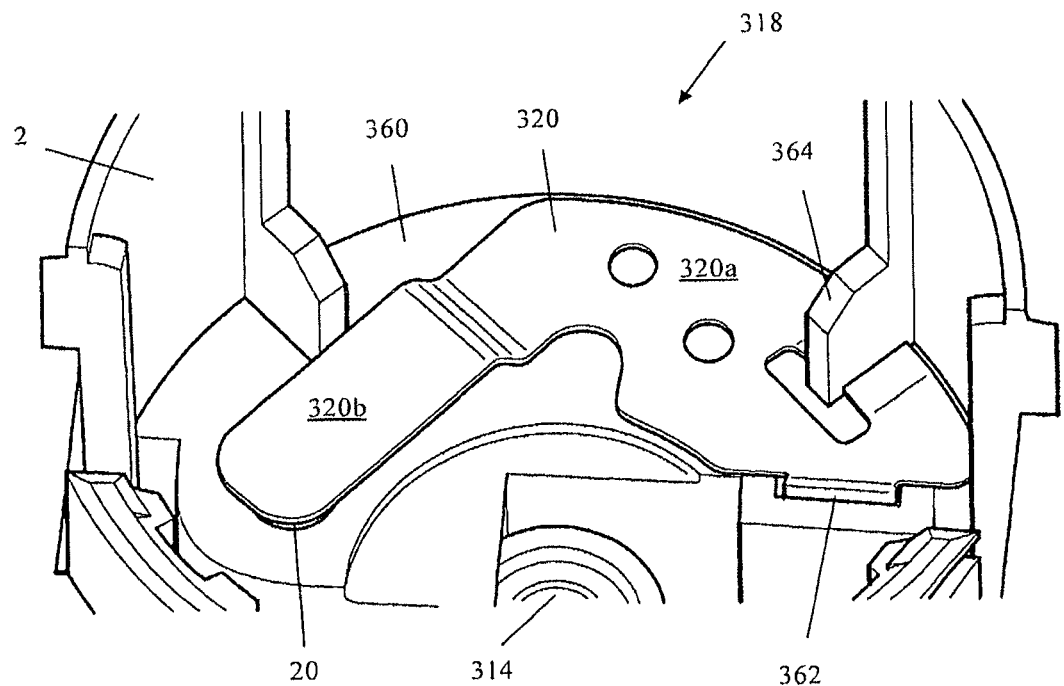
FIG. 11 is a perspective view of part of a third dose counter according to the present invention.
Figure 12:
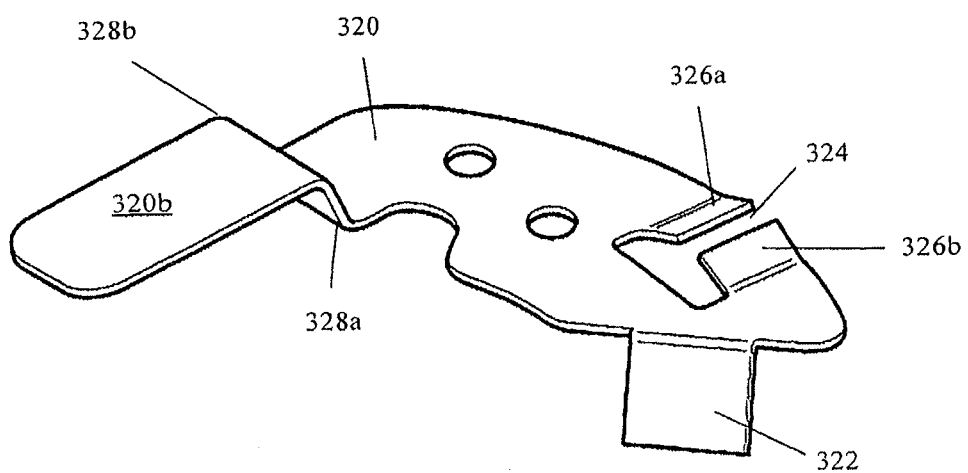
FIG. 12 is a perspective view of an element of the third dose counter shown in isolation.

In the third dose counter 318 the neutral position of the medicament canister (the position prior to depression) is raised slightly so that its ferrule is not in direct contact with the upper surface of the actuator shaft 20. This is achieved by raising the position of the stem block 314 relative to the components of the dose counter 318. The third dose counter 318 additionally comprises an actuator member 320 in the form of a stamped metal component arranged directly under the canister (not shown). The actuator member 320 is formed of a metal such as stainless steel to be resilient, that is to say elastically deformable. The actuator member 320 is arranged for engagement by the canister and is further arranged for engaging the upper surface of the actuator shaft 20. The actuator member 320 is shown in FIG. 11, which is a cut-away perspective view showing the inside of a breath-actuated inhaler body 2 without a medicament canister, and in FIG. 12, which shows the actuator member 320 in isolation.

The actuator member 320 defines two portions: a flat mounting structure 320a and an elongated lever 320b extending from the mounting structure 320a in a cantilever configuration. The mounting structure 320a is a flat base portion of the member 320 arranged to be mounted to the flat upper wall 360 of the dose counter chassis. The mounting structure 320a includes a folded-down tab 322 which passes through a slot 362 moulded into the chassis wall 360. The tab 322 serves to locate the member 320 in the correct position on the chassis wall 360. The mounting structure 320a also comprises an opening 324 provided with barb-like features 326a, 326b. A male locating feature 364 of the dose counter chassis passes through the opening 324 and the barb-like features 326a, 326b bear against the male locating feature 364 to retain the mounting structure 320a of the actuator member 320 in place against the chassis wall 360.

The lever 320b of the actuator member 320 extends from the mounting structure 320a. A proximal end of the lever 320b includes a pair of spaced apart bends 328a, 328b which space a distal end of the lever 320b from the chassis wall 360 in parallel spaced relationship. The distal end of the lever 320b is unsupported, thereby providing the lever 320b with the cantilever configuration. As shown in FIG. 11, the distal end of the lever 320a is positioned directly above the actuator shaft 20 of the dose counter 318.

As well as spacing the lever 320b from the chassis wall 360, the bends 328a, 328b serve as flexure hinges. More particularly, the bend 328a closest to the mounting structure 320a defines a pivotal mounting for the lever 320b. The other bend 328b serves as an input portion of the lever 320b and is able to flex to accommodate an overtravel condition of the medicament canister. Deformation of the flexure hinges is elastic, with the lever 320b returning to the neutral position shown in FIGS. 11 and 12 when all external loads are removed. The flexure hinges may be defined by portions of the lever 320b having reduced flexural strength, so that when the lever 320b is displaced the resulting flexing is confined to the flexure hinges.

Use of the third dose counter 318 for counting doses dispensed from a metered-dose inhaler will now be described with reference to FIGS. 13a to 13c, which are schematic sectional views showing the dose counter at different stages of actuation. The Figures show the actuator shaft 20 of the dose counter 318 together with the actuator member 320 described hereinabove. The components of the third dose counter 318 beneath the actuator member 320 are essentially the same as those shown in FIGS. 1 and 2 and are not illustrated in any detail. As described hereinabove, the bend 328a closest to the mounting structure 320a defines a pivotal mounting of the lever 320b. The other bend 328b defines an input portion of the lever 320b for engagement by the medicament canister (not shown). The distal end of the lever 320b defines an output portion of the lever 320b.

Figure 13A:
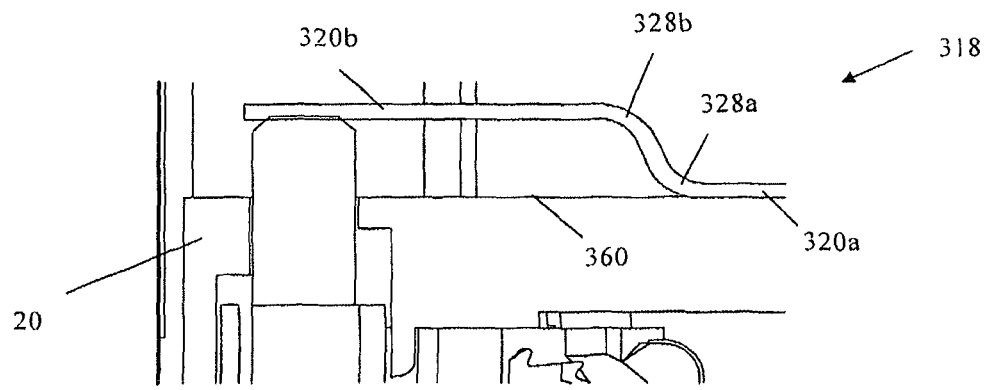
FIGS. 13a to 13c are schematic sectional views of the third dose counter for use in explaining its operation.
Figure 13B:
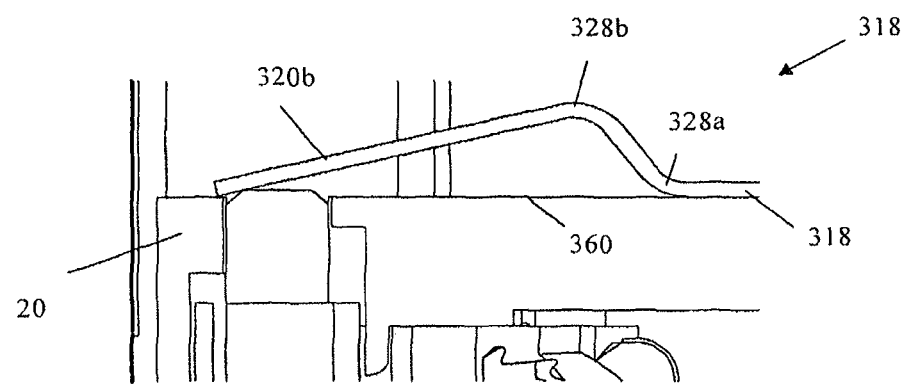

In FIG. 13a the dose counter 318 is shown in its neutral arrangement, that is to say the arrangement prior to depression of the medicament canister to dispense a dose of medicament. In this arrangement, the lever 320b is spaced from the upper wall of the dose counter chassis 360 in the cantilever configuration. The ferrule of the canister (not shown) is positioned slightly above the lever 320b and defines an engagement surface which extends parallel to the chassis wall 360. The actuator shaft 20 is biased into its uppermost position by compression spring 24 (see FIG. 1) and contacts the underside of the lever 320b.

The metered-dose inhaler is actuated by the user applying a manual compressive force to the closed end of the canister. In response to this compressive force, the canister moves axially with respect to its valve stem (not shown) by an amount varying between 2 and 4 mm. Approximately 2 mm of displacement is required to fire the valve and dispense a dose of medicament. The downwards movement of the canister causes the ferrule to engage with and displace downwards the input portion of the lever (defined by bend 328b), thereby causing the lever 320b to rotate counter-clockwise about the pivotal mounting (defined by bend 328a). The output portion of the lever (defined by the distal end) engages and displaces downwards the actuator shaft 20 against the compression spring 24 (see FIG. 1), as shown in FIG. 13b. Downwards displacement of the actuator shaft 20 increments the dose counter 318, as described hereinabove with reference to FIGS. 1 and 2.

The input portion of the lever (defined by bend 328b) is positioned between the pivotal mounting (defined by bend 328a) and the output portion of the lever (defined by the distal end), and is relatively closer to the pivotal mounting. As such, the lever serves to amplify a linear input stroke at the input portion so that the output portion provides an increased stroke for displacing the actuator shaft 20. In this way, the length of the stroke available for indexing the ratchet-toothed wheel 30 (see FIG. 2) is increased, as compared to dose counters of the type illustrated in FIGS. 1 to 4. This reduces the risk of miscounting, particularly undercounting, and, in turn, reduces the failure rate of the dose counter.

The amplification of the linear input stroke is particularly advantageous for manually operated metered-dose inhalers, since the linear input stroke with this type of inhaler may be as small as 1.5 mm when the medicament canister is released immediately after the fire point of the valve has been reached. The amplification of the linear input stroke can also reduce the risk of miscounting due to accumulated tolerance stacks and lost motion.

Figure 13C:
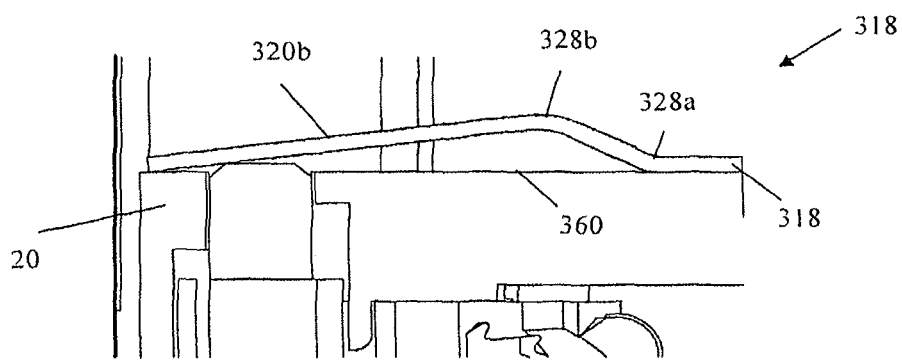

FIG. 13c shows the arrangement of the third dose counter 318 after the distal end of the lever 320b has reached the end of its downwards travel, and following further downwards displacement of the medicament canister (not shown). In this arrangement, the lever 320b has flexed at the bend 328b which defines the input portion of the lever 320b to thereby accommodate overtravel of the canister. As shown in the Figure, the lever 320b straightens out to allow the medicament canister to continue to move downwards without causing any further downwards displacement at the distal end of the lever 320b. The lever 320b is configured so that it only flexes to accommodate the overtravel after the distal end of the lever 320b has reached the end of its downwards travel.

Figure 14:
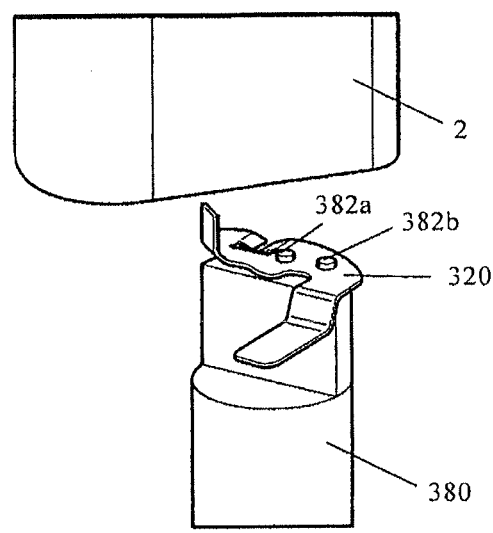
FIG. 14 illustrates the installation of the element shown in FIG. 12 into the body of a metered-dose inhaler.

FIG. 14 illustrates part of a method for assembling the third dose counter 318 into a metered-dose inhaler. According to the method, the actuator member 320 is inserted into the inhaler body 2 before the medicament canister. As shown in the Figure, the actuator member 320 is mounted on a mandrel 380 and held in place by pins 382a, 382b which engage a pair of holes formed in the actuator member 320, The inhaler body 2 is then lowered over the mandrel 380 until the male locating feature 364 inside the inhaler body 2 is engaged by the barb-like features 326a, 326b of the actuator member 320 (see FIGS. 11 and 12). The mandrel 380 is then withdrawn to leave the actuator member 320 installed in the inhaler body 2, following which the medicament canister (not shown) is inserted.

A fourth dose counter 418 according to the present invention will now be described with reference to FIGS. 15 to 18. The fourth dose counter 418 is the same as the third dose counter described hereinabove, except that it has a modified dose counter chassis and is provided with a different actuator member 420. The description of the fourth dose counter 418 will therefore mainly be limited to these elements.

In common with the third dose counter, the actuator member 420 of the fourth dose counter 418 is a stamped metal component arranged directly under the medicament canister (not shown). The actuator member 420 is formed of a metal such as stainless steel to be resilient, that is to say elastically deformable. The actuator member 420 is arranged for engagement by the canister and is further arranged for engaging the upper surface of the actuator shaft 20. The actuator member 420 is shown in FIG. 15, which is a cut-away perspective view showing the inside of a breath-actuated inhaler body 2 without a medicament canister, and in FIG. 16, which shows the actuator member 420 in isolation.

The actuator member 420 of the fourth dose counter 418 includes an elongated lever 420a which is pivotally mounted to the upper wall 460 of the dose counter chassis. The pivotal mounting is provided by a narrow tongue 420b which is extended from one end of the lever 420a and passes through a slot (hidden in FIG. 15) formed in the chassis wall 460. The chassis wall 460 is stepped, as shown in FIG. 15, and the slot is formed along the internal corner defined by the step. The slot is formed in a relatively thin portion of the chassis wall 460, which allows the actuator member 420 to rotate about the end of the lever 420a. The end of lever 420a bears against the stepped chassis wall 460 and defines the pivot point.

Figure 15:
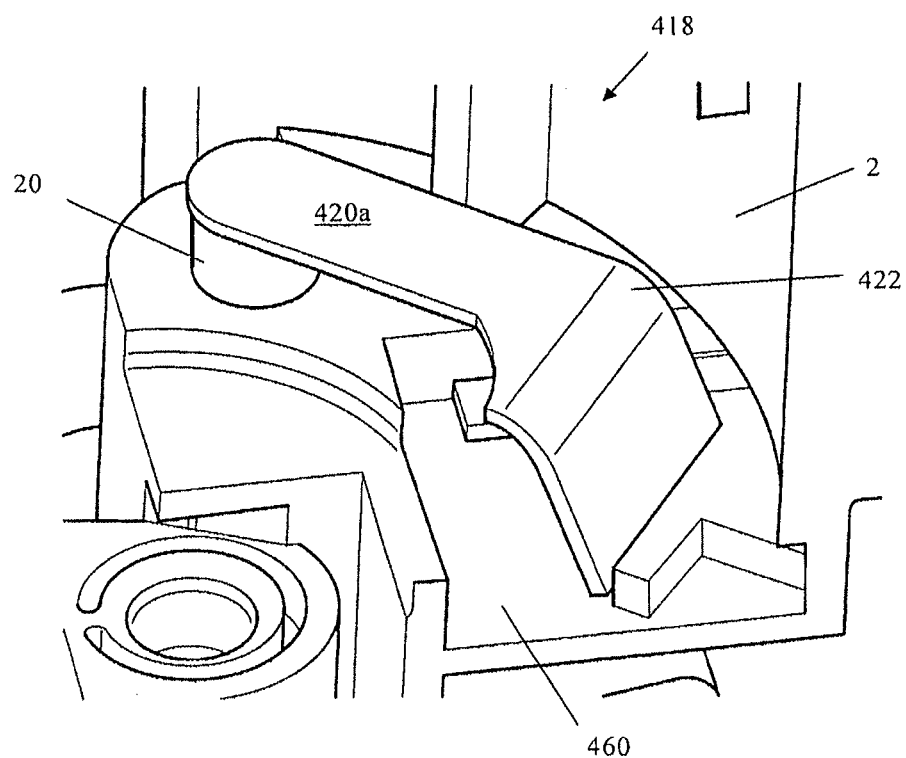
FIG. 15 is a perspective view of part of a fourth dose counter according to the present invention.
Figure 16:
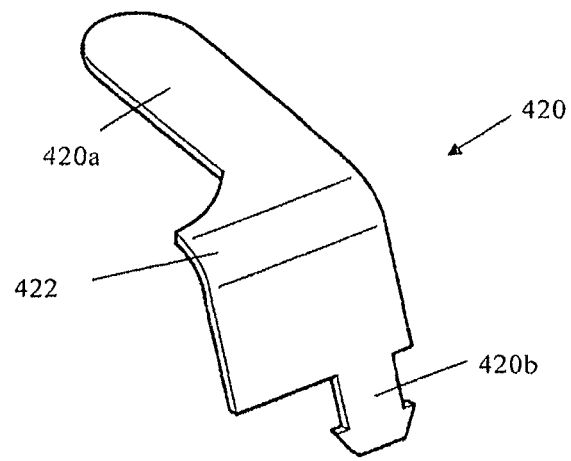
FIG. 16 is a perspective view of an element of the fourth dose counter shown in isolation.

As shown in FIG. 15, the lever 420a of the actuator member 420 extends from the pivotal mounting and is provided with a bend 422. The distal end of the lever 420a is positioned directly above the actuator shaft 20. The bend 422 spaces the distal end of lever 420a from the chassis wall 460 in parallel spaced relationship. The bend 422 also serves as an input portion of the lever 420a and defines a flexure hinge for accommodating an overtravel condition of the medicament canister. Deformation of the flexure hinge is elastic, with the lever 420b returning to the neutral shape shown in FIGS. 15 and 16 when all external loads are removed. The flexure hinge may be defined by a portion of the lever 420a having reduced flexural strength, so that when the lever 420a is displaced the resulting flexing is confined to the flexure hinge.

Compared to the actuator member of the third dose counter, which includes two flexure hinges, the actuator member 420 of the fourth dose counter only has one flexure hinge. In this way the design of the actuator member 420 is simplified. Furthermore, the amount of flexure of the lever 420a required to accommodate overtravel of the medicament canister may be reduced by providing the stepped chassis wall 460.

Use of the fourth dose counter 418 for counting doses dispensed from a metered-dose inhaler will now be described with reference to FIGS. 17a to 17c, which are schematic sectional views showing the dose counter at different stages of actuation. The Figures show the actuator shaft 20 of the dose counter 418 together with the actuator member 420 described hereinabove. The components of the fourth dose counter 418 beneath the actuator member 420 are essentially the same as those shown in FIGS. 1 and 2 and are not illustrated in any detail. As described hereinabove, the end of the lever 420a closest to the tongue 420b defines the pivotal mounting of the lever 420a. The bend 422 defines an input portion of the lever 420a for engagement by the medicament canister (not shown). The distal end of the lever 420a defines an output portion of the lever 420a.

Figure 17A:
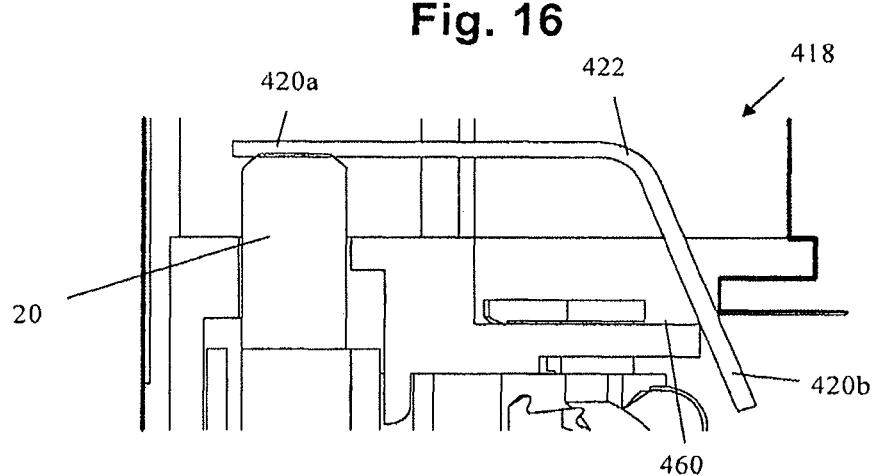
FIGS. 17a to 17c are schematic sectional views of the fourth dose counter for use in explaining its operation.
Figure 17B:
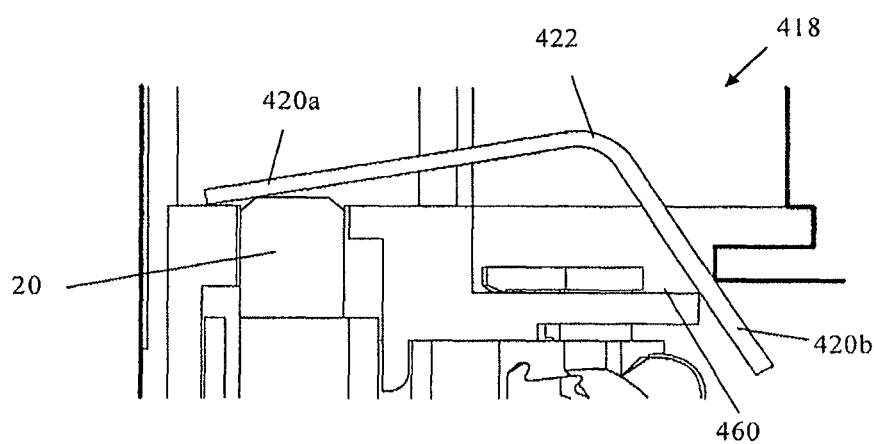

In FIG. 17a the dose counter 418 is shown in its neutral arrangement, that is to say the arrangement prior to depression of the medicament canister to dispense a dose of medicament. In this arrangement, the distal end of the lever 420a is spaced from the upper wall of the dose counter chassis 460. The ferrule of the canister (not shown) is positioned slightly above the lever 420a and defines an engagement surface which extends parallel to the chassis wall 460. The actuator shaft 20 is biased into its uppermost position by compression spring 24 (see FIG. 1) and contacts the underside of the lever 420a.

The metered-dose inhaler is actuated by the user applying a manual compressive force to the closed end of the canister. In response to this compressive force, the canister moves axially with respect to its valve stem (not shown) by an amount varying between 2 and 4 mm. Approximately 2 mm of displacement is required to fire the valve and dispense a dose of medicament. The downwards movement of the canister causes the ferrule to engage with and displace downwards the input portion of the lever (defined by bend 422), thereby causing the lever 420a to rotate counter-clockwise about the pivotal mounting. The output portion of the lever (defined by the distal end) engages and displaces downwards the actuator shaft 20 against the compression spring 24 (see FIG. 1), as shown in FIG. 17b. Downwards displacement of the actuator shaft 20 increments the dose counter 418, as described hereinabove with reference to FIGS. 1 and 2.

The input portion of the lever (defined by bend 422) is positioned between the pivotal mounting and the output portion of the lever (defined by the distal end), and is relatively closer to the pivotal mounting. As such, the lever 420a serves to amplify a linear input stroke at the input portion so that the output portion provides an increased stroke for displacing the actuator shaft 20. In this way, the length of the stroke available for indexing the ratchet-toothed wheel 30 (see FIG. 2) is increased as compared to dose counters of the type illustrated in FIGS. 1 to 4. This reduces the risk of miscounting, particularly undercounting, and, in turn, reduces the failure rate of the dose counter.

Figure 17C:
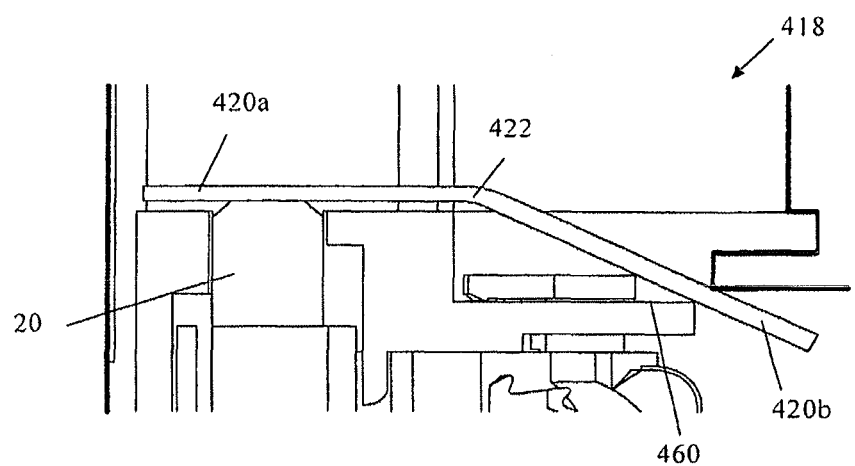

FIG. 17c shows the arrangement of the fourth dose counter 418 after the distal end of the lever 420a has reached the end of its downwards travel, and following further downwards displacement of the medicament canister (not shown). In this arrangement, the lever 420a has flexed at the bend 422 which defines the input portion of the lever 420a to thereby accommodate overtravel of the canister. As shown in the Figure, the lever 420a straightens out to allow the medicament canister to continue to move downwards without causing any further downwards displacement at the distal end of the lever 420a. The lever 420a is configured so that it only flexes to accommodate the overtravel after the distal end of the lever 420a has reached the end of its downwards travel.

Figure 18:
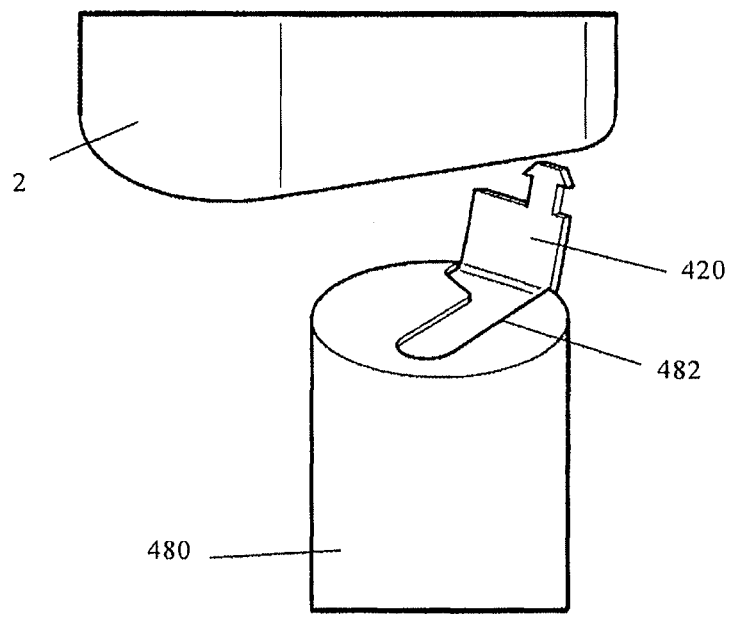
FIG. 18 illustrates the installation of the element shown in FIG. 16 into the body of a metered-dose inhaler.

FIG. 18 illustrates part of a method for assembling the fourth dose counter 418 described hereinabove into a metered-dose inhaler. According to the method, the actuator member 420 is inserted into the inhaler body 2 before the medicament canister. As shown in the Figure, the actuator member 420 is mounted on a mandrel 480 and held in place in a recess 422 formed in the end surface of the mandrel 480. The inhaler body 2 is then lowered over the mandrel 480 until the tongue 420b of the actuator member 420 has passed through the slot in the upper wall 460 of the dose counter chassis (see FIGS. 15 and 16). The mandrel 480 is then withdrawn to leave the actuator member 420 installed in the inhaler body 2, following which the medicament canister (not shown) is inserted.

Figure 19:
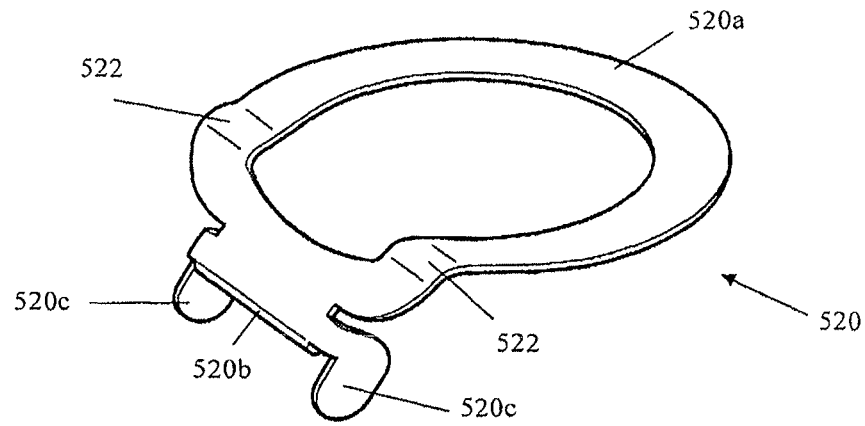
FIG. 19 is a view of a variation to the element shown in FIG. 16 for use in a fifth dose counter according to the present invention.
Figure 20:
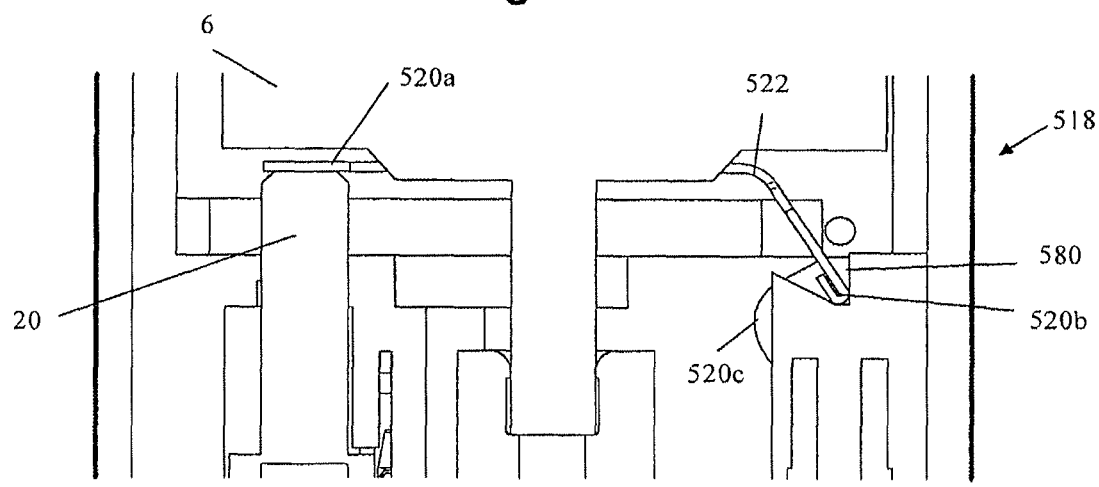
FIG. 20 is a schematic sectional view of the fifth dose counter for use in explaining its operation.

FIGS. 19 and 20 show an alternative actuator member design for use in a fifth dose counter 518 according to the present invention. The modified actuator member 520 differs from the actuator member of the fourth dose counter in that the lever 520a has an annular shape instead of an elongated shape, with the bend 522 being provided on both sides of the lever 520a. The actuator member 520 is assembled into the fifth dose counter 518 with the annular lever 520a being approximately concentric with the medicament canister 6, as illustrated in the schematic sectional view of FIG. 20.

The modified actuator member 520 also differs from the actuator member of the fourth dose counter in that the pivotal mounting of the lever 520a is defined by a straight edge 520b of the member 520. The edge 520b of the modified member 520 is located in and bears against a "V" shaped channel 580 formed in the chassis of the dose counter 518. The edge 520b of the modified member 520 includes a hem bend to provide a smooth bearing surface, as shown in FIG. 20. The modified member 520 also includes a pair of alignment tabs 520c which extend in a direction perpendicular to the edge 520b. The alignment tabs 520c are received into corresponding slots in the "V" shaped channel 580 of the dose counter chassis and locate the actuator member 520 in the length direction of the channel 580. The actuator member 520 is retained in the inhaler body 2 by the medicament canister 6, as shown in FIG. 20.

The fifth dose counter 518 functions in the same way as the fourth dose counter described hereinabove. A detailed description of use of the fifth dose counter 518 will therefore be omitted.

Figure 21:
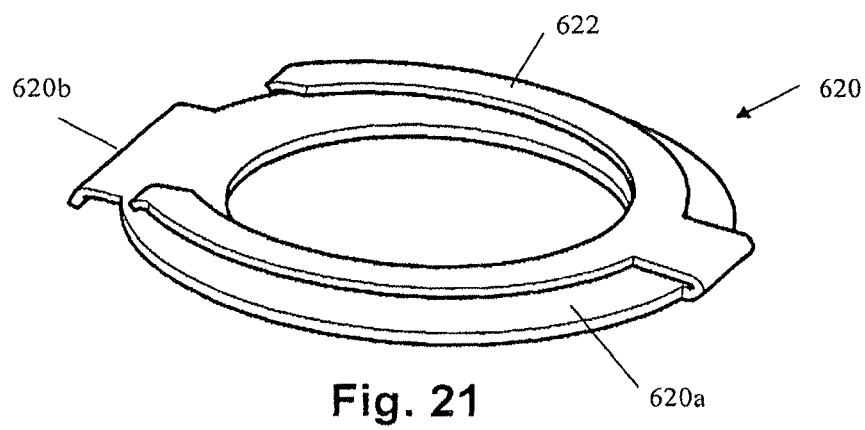
FIG. 21 is a view of another variation to the element shown in FIG. 16 for use in a sixth dose counter according to the present invention.
Figure 22A:
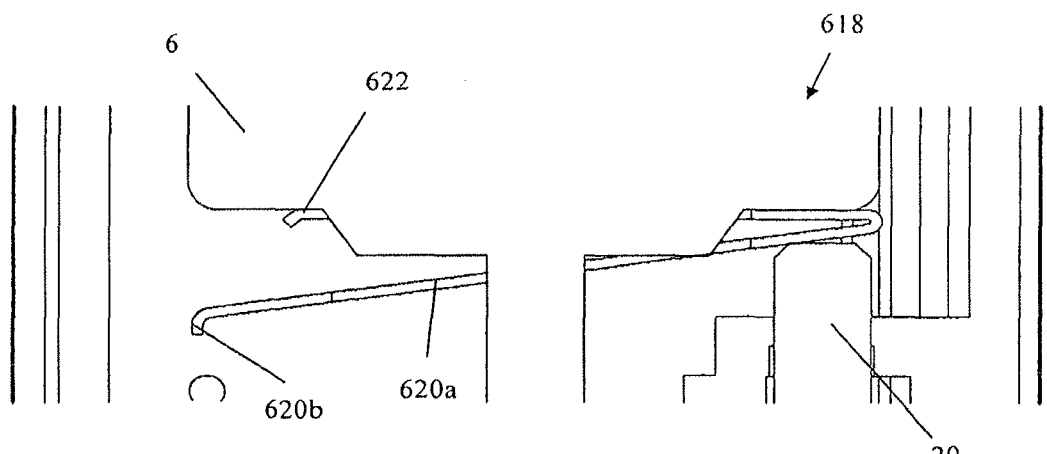
FIGS. 22a to 22c are schematic sectional views of the sixth dose counter for use in explaining its operation.
Figure 22B:
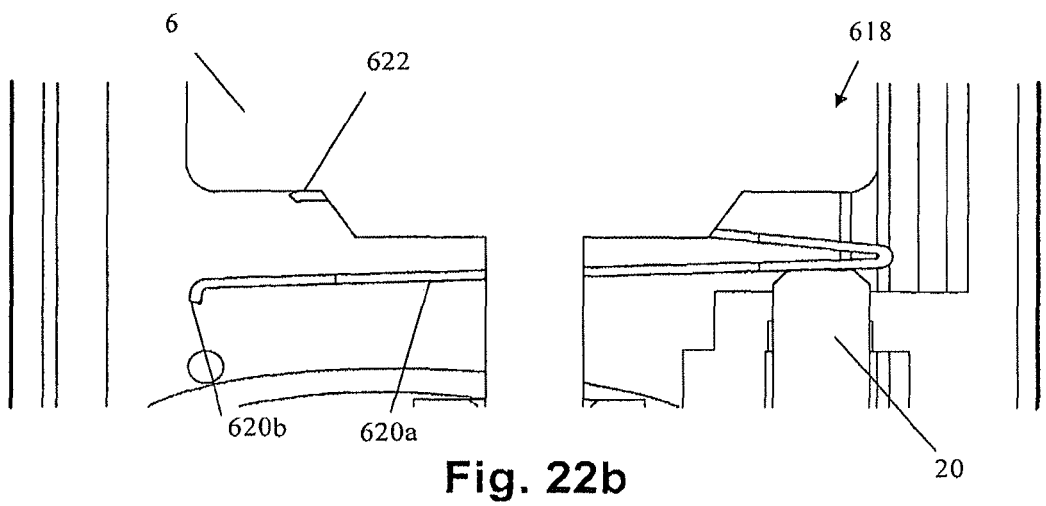
Figure 22C:
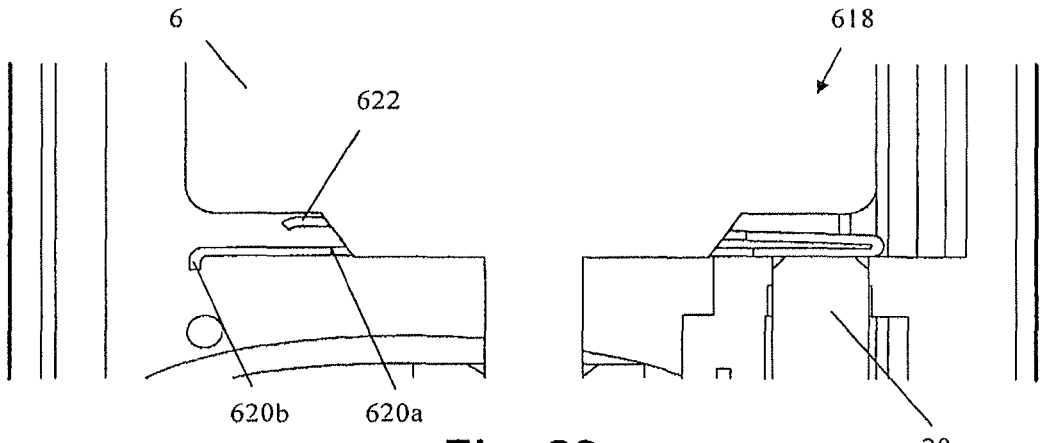
Figure 23:
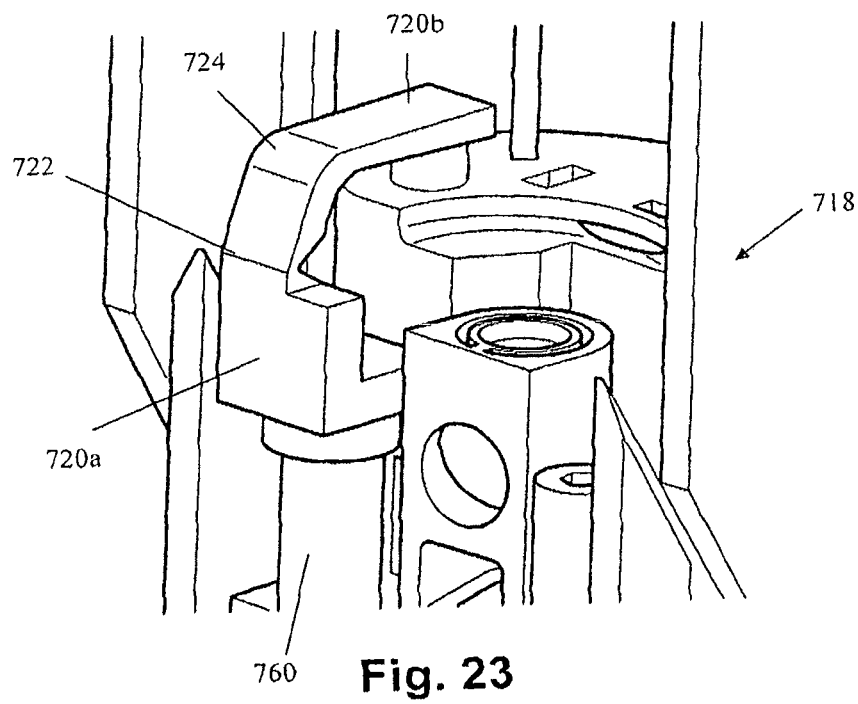
FIG. 23 is a perspective view of part of a seventh dose counter according to the present invention.
Figure 24:
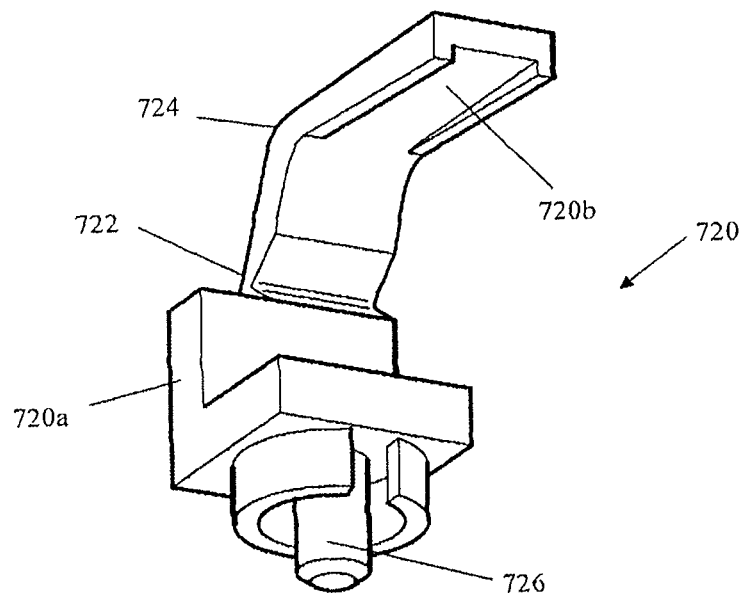
FIG. 24 is a perspective view of an element of the seventh dose counter shown in isolation.

FIGS. 21 to 22c show another alternative actuator member design for use in a sixth dose counter 618 according to the present invention. The modified actuator member 620 differs from the actuator member of the fifth dose counter in that the lever 620a is not provided with a bend, but instead has a "clamshell" configuration. Thus, the distal end of the lever 620a is provided with a forked spring element 622 which extends from the distal end of the lever 620a and is folded over the upper surface of the lever 620a to define an acute angle therewith. The actuator member 620 is assembled into the sixth dose counter 618 with both the annular lever 520a and the forked spring element 622 being approximately concentric with the medicament canister 6, as illustrated in the schematic sectional views of FIGS. 22a to 22c.

A distal end of the forked spring element 622 defines the input portion of the lever 620a. The distal end of the lever 620a, which is also a proximal end of the spring element 622, defines the output portion of the lever 620a. The actuator member 620 is also provided with a flat edge 620b which defines the pivotal mounting of the lever 620a, as illustrated in the Figures.

Use of the sixth dose counter 618 for counting doses dispensed from a metered-dose inhaler will now be described with reference to FIGS. 22a to 22c, which are schematic sectional views showing the dose counter at different stages of actuation. The Figures show the actuator shaft 20 of the dose counter 618 together with the actuator member 620 described hereinabove. The components of the sixth dose counter 618 beneath the actuator member 620 are essentially the same as those shown in FIGS. 1 and 2 and are not illustrated in any detail.

In FIG. 22a the dose counter 618 is shown in its neutral position, that is to say the position prior to depression of the medicament canister to dispense a dose of medicament. In this position, the ferrule of the canister 6 is positioned above the forked spring element 622. The actuator shaft 20 is biased into its uppermost position by compression spring 24 (see FIG. 1) and contacts the underside of the lever 620a.

The metered-dose inhaler is actuated by the user applying a manual compressive force to the closed end of the canister 6. In response to this compressive force, the canister 6 moves axially with respect to its valve stem (not shown) by an amount varying between 2 and 4 mm. The downwards movement of the canister 6 causes the ferrule to displace downwards the input portion of the lever (defined by the distal end of the spring element 622), thereby causing the lever 620a to rotate clockwise about the pivotal mounting (defined by edge 620b). The output portion of the lever (defined by the distal end of the lever 620a) engages and displaces downwards the actuator shaft 20 against the compression spring 24 (see FIG. 1), as shown in FIG. 22b. Downwards displacement of the actuator shaft 20 increments the dose counter 618, as described hereinabove with reference to FIGS. 1 and 2. The spring element 622 is configured such that it does not deform significantly during actuation of the dose counter 618.

The input portion of the lever (defined by the distal end of the spring element 622) is positioned between the pivotal mounting and the output portion (defined by the distal end of the lever 620a), and is relatively closer to the pivotal mounting. As such, the lever 620a serves to amplify a linear input stroke at the input portion so that the output portion provides an increased stroke for displacing the actuator shaft 20. In this way, the length of the stroke available for indexing the ratchet-toothed wheel 30 (see FIG. 2) is increased as compared to dose counters of the type illustrated in FIGS. 1 to 4. This reduces the risk of miscounting, particularly undercounting, and, in turn, reduces the failure rate of the dose counter.

FIG. 22c shows the arrangement of the sixth dose counter 618 after the distal end of the lever 620a has reached the end of its downwards travel, and following further downwards displacement of the medicament canister 6. In this arrangement, the spring element 622 has yielded to thereby accommodate overtravel of the canister 6. As shown in the Figure, the spring element 622 is displaced towards the lever 620a to allow the medicament canister 6 to continue to move downwards without causing any further downwards displacement at the distal end of the lever 620a. The spring element 622 is configured so that it only yields to accommodate the overtravel after the distal end of the lever 420a has reached the end of its downwards travel.

FIGS. 23 to 25c show yet another alternative actuator member design for use in a seventh dose counter 718 according to the present invention. The modified actuator member 720 is similar to the actuator member of the third dose counter except that, instead of being a stamped metal component, it is a moulded plastics component. Thus, the actuator member 720 comprises an integrally formed mounting structure 720a and elongated lever 720b. The mounting structure 720a and the lever 720b are separated from each other by a living hinge 722 which defines a pivotal mounting for the lever 720b. The lever 720b is provided with a bend 724, which bend also serves as a flexure hinge. The actuator member 720 also includes a mounting post 726 which is received in a hexagonal opening in the dose counter chassis 760 with an interference fit. The actuator member 720 is mounted to the dose counter chassis 760 such that the distal end of the lever 720a is positioned over the actuator shaft 20.

Use of the seventh dose counter 718 for counting doses dispensed from a metered-dose inhaler will now be described with reference to FIGS. 25a to 25c, which are schematic sectional views showing the dose counter at different stages of actuation. The Figures show the actuator shaft 20 of the dose counter 718 together with the actuator member 720 described hereinabove. The components of the seventh dose counter 718 beneath the actuator member 720 are essentially the same as those shown in FIGS. 1 and 2 and are not illustrated in any detail. As described hereinabove, the living hinge 722 defines a pivotal mounting of the lever 720b. The bend 724 defines an input portion of the lever 720b for engagement by the medicament canister (not shown). The distal end of the lever 720b defines an output portion of the lever 720b.

Figure 25A:
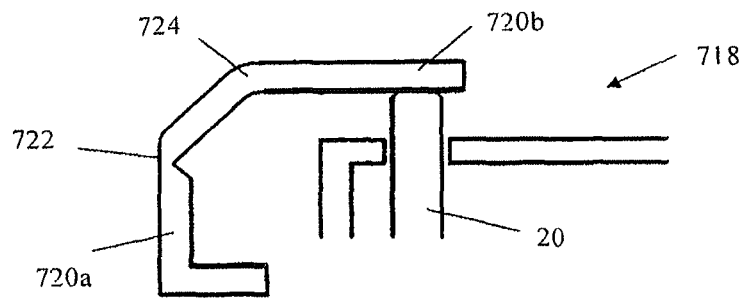
FIGS. 25a to 25c are schematic sectional views of the seventh dose counter for use in explaining its operation.
Figure 25B:
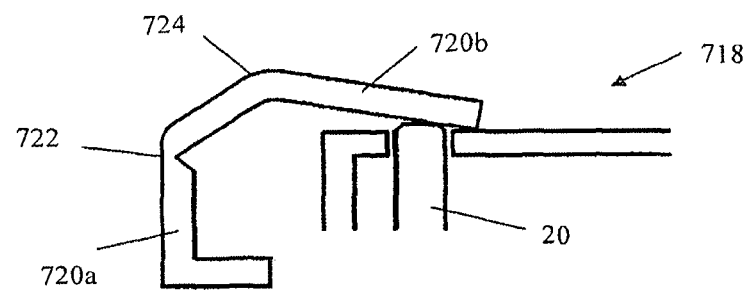

In FIG. 25a the dose counter 718 is shown in its neutral arrangement, that is to say the arrangement prior to depression of the medicament canister to dispense a dose of medicament. The ferrule of the canister (not shown) is positioned slightly above the lever 720b. The actuator shaft 20 is biased into its uppermost position by compression spring 24 (see FIG. 1) and contacts the underside of the lever 720b.

The metered-dose inhaler is actuated by the user applying a manual compressive force to the closed end of the canister. In response to this compressive force, the canister moves axially with respect to its valve stem (not shown) by an amount varying between 2 and 4 mm. The downwards movement of the canister causes the ferrule to engage with and displace downwards the input portion of the lever (defined by the bend 724), thereby causing the lever 720b to rotate clockwise about the pivotal mounting (defined by the living hinge 722). The output portion of the lever (defined by the distal end) engages and displaces downwards the actuator shaft 20 against the compression spring 24 (see FIG. 1), as shown in FIG. 25b. Downwards displacement of the actuator shaft 20 increments the dose counter 718, as described hereinabove with reference to FIGS. 1 and 2.

The input portion of the lever (defined by the bend 724) is positioned between the pivotal mounting (defined by the living hinge 722) and the output portion of the lever (defined by the distal end), and is relatively closer to the pivotal mounting. As such, the lever serves to amplify a linear input stroke at the input portion so that the output portion provides an increased stroke for displacing the actuator shaft 20. In this way, the length of the stroke available for indexing the ratchet-toothed wheel 30 (see FIG. 2) is increased as compared to dose counters of the type illustrated in FIGS. 1 to 4. This reduces the risk of miscounting, particularly undercounting, and, in turn, reduces the failure rate of the dose counter.

Figure 25C:
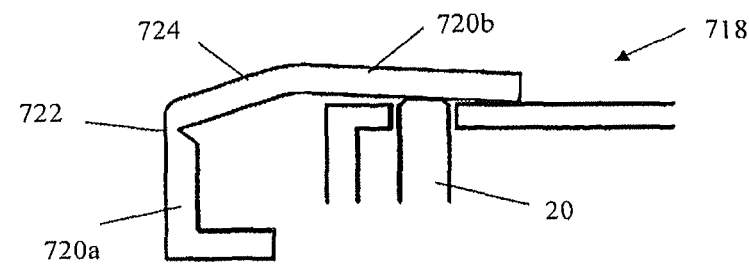

FIG. 25c shows the arrangement of the seventh dose counter 718 after the distal end of the lever 720b has reached the end of its downwards travel, and following further downwards displacement of the medicament canister (not shown). In this arrangement, the lever 720b has flexed at the bend 724 to thereby accommodate overtravel of the canister. As shown in the Figure, the lever 720b straightens out to allow the medicament canister to continue to move downwards without causing any further downwards displacement at the distal end of the lever 720b. The lever 720b is configured so that it only flexes to accommodate the overtravel after the distal end of the lever 720b has reached the end of its downwards travel. The flexure at the bend 724 is elastic, such that the lever 720b returns to its neutral shape as shown in FIGS. 25b and 25c when the external loads are removed.

FIGS. 26 to 28c show yet another alternative actuator member design for use in an eighth dose counter 818 according to the present invention. The modified actuator member 820 is similar to the actuator member of the fifth dose counter except that, instead of being a flexible metal component, it is provided as a rigid metal component. Instead of having a flexure hinge for accommodating overtravel of the medicament canister 6, the modified actuator member 820 is provided with a pivotal mounting which can be displaced downwards against a resilient bias to accommodate the overtravel.

Figure 26:
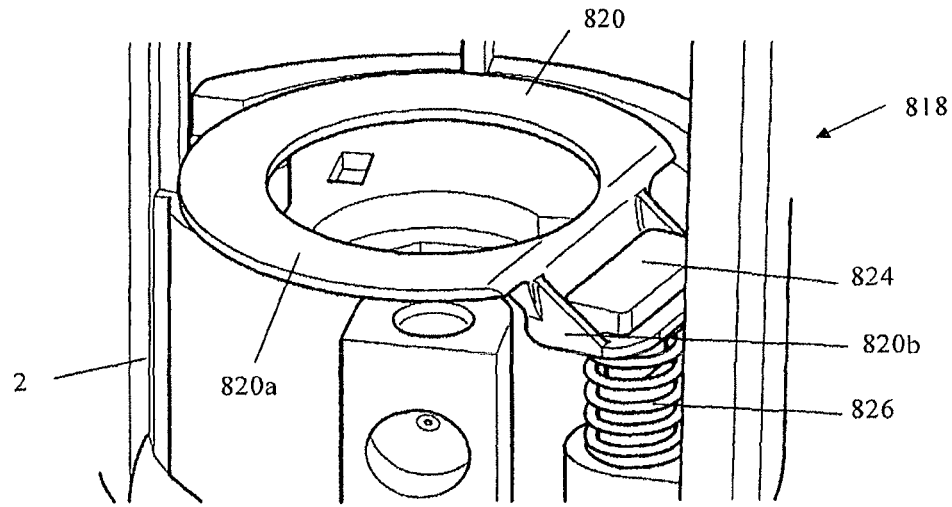
FIG. 26 is a perspective view of part of an eighth dose counter according to the present invention.

FIG. 26 is a cut-away perspective view of a metered-dose inhaler in which elements of the eighth dose counter 818 are visible. The actuator member 820 includes an annular lever 820a and a protrusion 820b which extends from the annular lever 820a in a radially outwards direction. A step is defined between the annular lever 820a and the protrusion 820b, as shown in the Figure. A square through-hole is formed in the protrusion 820b and defines a pivotal mounting for the lever 820a. The actuator member 820 is installed in the body 2 of the metered-dose inhaler to be approximately concentric with the medicament canister (not shown).

A fixed mounting post 824 extends from the inhaler body 2 in a direction parallel to the actuator shaft 20 of the dose counter 818. The mounting post 824 has a "T" shaped head and passes through the hole formed in the protrusion 820b of the actuator member 820. The hole is sized to be larger than the cross-section of the mounting post 824, so that the lever 820a is able to move up and down the post 824 and pivot about the post 824. The hole may be provided with rounded edges to prevent binding against the surface of the mounting post 824. The mounting post 824 caries a preloaded compression spring 826 which biases the actuator member 820 against the underside of the "T" shaped head. The underside of the "T" shaped head is provided with a rounded surface to help define the pivot point of the lever 820a.

Figures 27A, 27B:
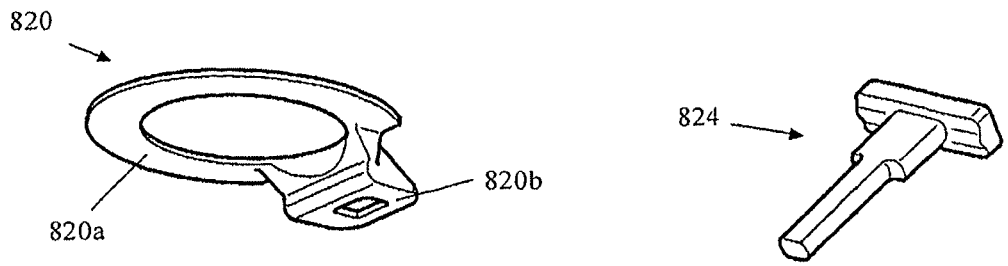
FIGS. 27a and 27b are perspective views of elements of the eighth dose counter shown in isolation.

The actuator member 820 and the mounting post 824 are shown more clearly in FIGS. 27a and 27b, respectively. The mounting post 824 is a rigid moulded plastics component.

Use of the eighth dose counter 818 for counting doses dispensed from a metered-dose inhaler will now be described with reference to FIGS. 28a to 28c, which are schematic sectional views showing the dose counter at different stages of actuation. The Figures show the actuator shaft 20 of the dose counter 818 together with the actuator member 820 and mounting post 824 described hereinabove. The components of the eighth dose counter 818 beneath the actuator member 820 are essentially the same as those shown in FIGS. 1 and 2 and are not illustrated in any detail.

As described hereinabove, the actuator member 820 includes a pivotally mounted lever 820a. The hole formed in the protrusion 820b defines the pivotal mounting of the lever 820a. The step between the lever 820a and the protrusion 820b defines an input portion of the lever 820a. The distal end of the lever 820a defines an output portion of the lever.

Figure 28A:
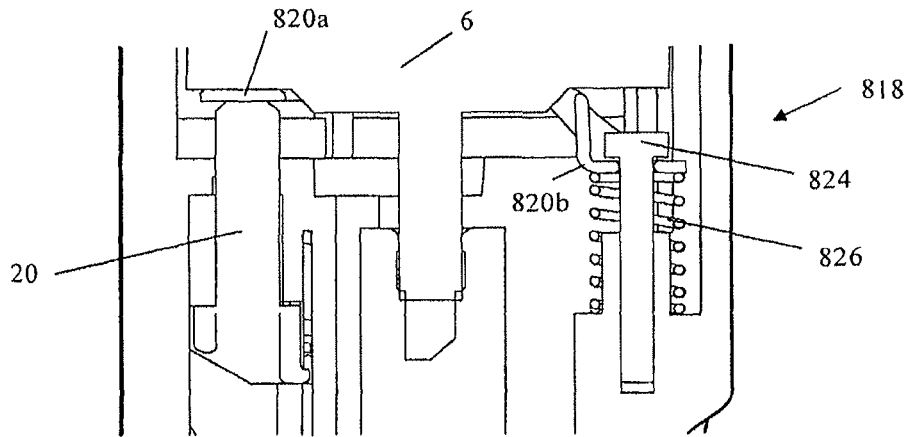
FIGS. 28a to 28c are schematic sectional views of the eighth dose counter for use in explaining its operation.
Figure 28B:
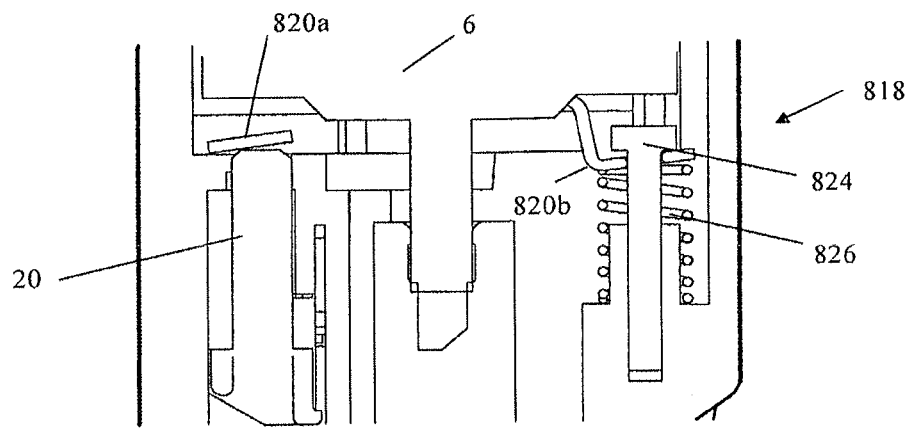

In FIG. 28a the dose counter 818 is shown in its neutral arrangement, that is to say the arrangement prior to depression of the medicament canister 6 to dispense a dose of medicament. The ferrule of the canister 6 is positioned directly above the lever. The pivotal mounting of the lever is biased into its uppermost position by compression spring 826. The actuator shaft 20 is also biased into its uppermost position by compression spring 24 (see FIG. 1) and contacts the underside of the lever 820a.

The metered-dose inhaler is actuated by the user applying a manual compressive force to the closed end of the canister 6. In response to this compressive force, the canister 6 moves axially with respect to its valve stem by an amount varying between 2 and 4 mm. The downwards movement of the canister 6 causes the ferrule to engage with and displace downwards the input portion of the lever (defined by the step in the actuator member 820), thereby causing the lever to rotate counter-clockwise about the pivotal mounting. The output portion of the lever (defined by the distal end) engages and displaces downwards the actuator shaft 20 against the compression spring 24 (see FIG. 1), as shown in FIG. 28b. Downwards displacement of the actuator shaft 20 increments the dose counter 818, as described hereinabove with reference to FIGS. 1 and 2.

The input portion of the lever (defined by the step in the actuator member 820) is positioned between the pivotal mounting and the output portion of the lever, and is relatively closer to the pivotal mounting. As such, the lever serves to amplify a linear input stroke at the input portion so that the output portion provides an increased stroke for displacing the actuator shaft 20. In this way, the length of the stroke available for indexing the ratchet-toothed wheel 30 (see FIG. 2) is increased as compared to dose counters of the type illustrated in FIGS. 1 to 4. This reduces the risk of miscounting, particularly undercounting, and, in turn, reduces the failure rate of the dose counter.

Figure 28C:
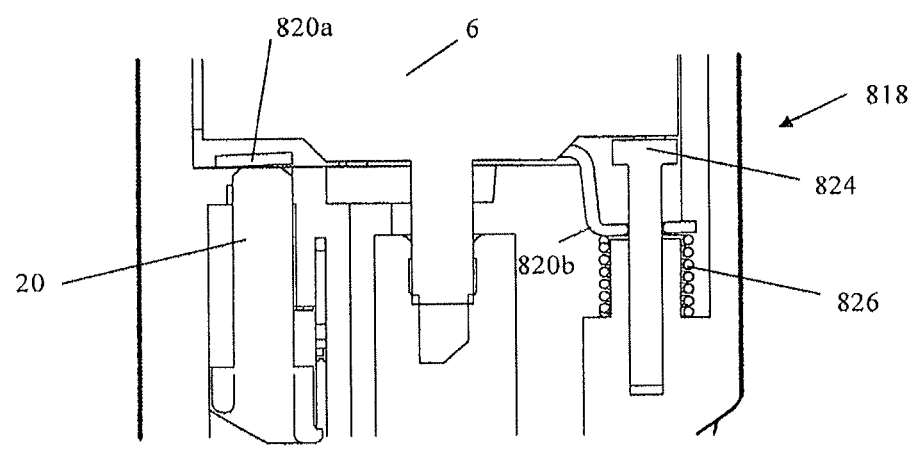

FIG. 28c shows the arrangement of the eighth dose counter 818 after the distal end of the lever 820a has reached the end of its downwards travel, and following further downwards displacement of the medicament canister 6. In this arrangement, the pivotal mounting of the lever (defined by the hole in the protrusion 820b) has been displaced downwards against the bias of compression spring 826, to thereby accommodate overtravel of the canister 6. As shown in the Figure, the pivotal mounting is displaced to allow the medicament canister 6 to continue to move downwards without causing any further downwards displacement at the distal end of the lever 820a. The preload of the compression spring 826 is configured so that it only yields to accommodate the canister overtravel after the distal end of the lever 820a has reached the end of its downwards travel.

A ninth dose counter according to the present invention will now be described with reference to FIGS. 29 to 30b. The ninth dose counter 918 is closely based on the dose counter 18 shown in FIGS. 1 and 2. Thus, the ninth dose counter 918 includes most of the components of the counter shown in FIGS. 1 and 2, including the ratchet-toothed wheel 30, the spindles 36, 40 and the flexible tape 44. A detailed description of these components of the ninth dose counter 918 will therefore be omitted, except to the extent that their form or function differs from that described hereinabove. The ninth dose counter 918 differs from the counter shown in FIGS. 1 and 2 in that the actuator shaft 20 is replaced with a pivotally mounted actuator member 920 carrying a driver for directly engaging the ratchet-toothed wheel 30. The actuator member 920 serves as a lever and is provided as a rigid moulded plastics component.

Figure 29:
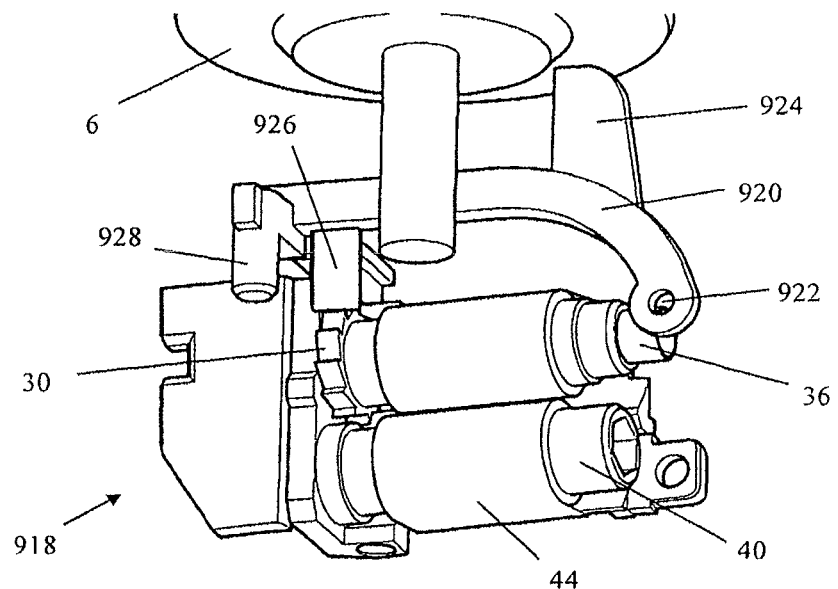
FIG. 29 is a perspective view of part of a ninth dose counter according to the present invention.
Figure 30A:
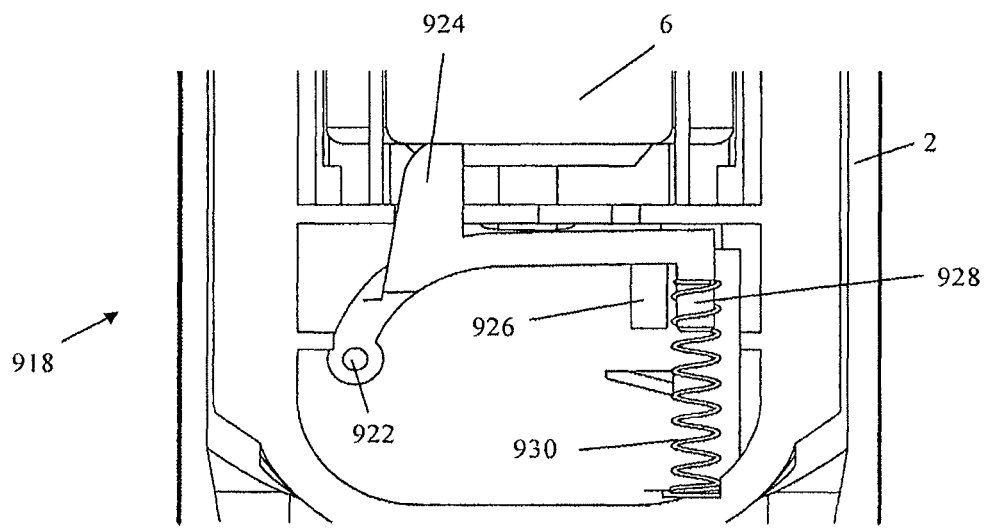
FIGS. 30a and 30b are schematic sectional views of the ninth dose counter for use in explaining its operation.
Figure 30B:
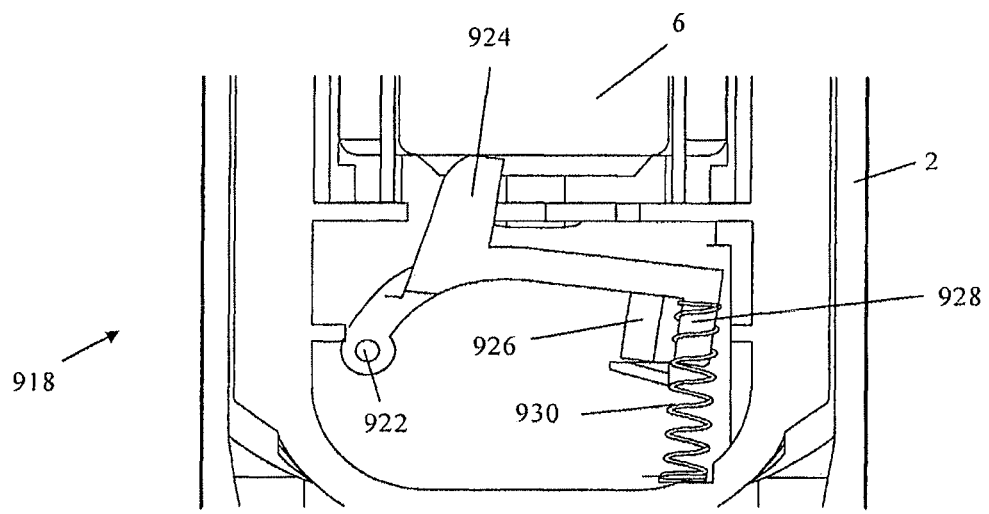

The actuator member 920 is shown in FIG. 29, which is a perspective view showing certain elements of the ninth dose counter 918, and in FIGS. 30a and 30b, which are schematic sectional views showing the ninth dose counter 918 at different stages of actuation. FIG. 29 and FIGS. 30a and 30b show opposite sides of the doe counter 918.

The actuator member 920 is provided at a first end with through-hole 922 about which the member is rotatably mounted to a pin (not shown) formed in the body 2 of the metered-dose inhaler. The member 920 is rotatably mounted such that an axis of rotation is perpendicular to the axis of the medicament canister 6. The first end of the member 920 has a generally arcuate shape. An intermediate portion of the actuator member 920 is provided with an upwardly extending protrusion 924 which serves as an input portion of the lever for engagement by the ferrule of the medicament canister 6. The protrusion 924 is provided with a rounded edge so that, when the protrusion is engaged by the downwardly-moving ferrule, the rounded edge slides smoothly across surface of the ferrule.

A second end of the actuator member 920 is provided with a downwardly extending spigot 928 onto which the upper end of a compression spring 930 is mounted for biasing the member 920 towards the medicament canister 6. The second end of the member 920 is also provided with a downwardly extending protrusion 926 which carries a driver for rotatably driving the ratchet-toothed wheel 30. The driver comprises a ratchet drive pawl arranged to directly engage the teeth of the ratchet-toothed wheel 30 on a downwards stroke of the actuator member 920. The second end of the member 920 is generally straight.

Use of the ninth dose counter 318 for counting doses dispensed from a metered-dose inhaler will now be described with reference to FIGS. 30a and 30b. The Figures show the medicament canister 6 of the inhaler, together with the actuator member 920 described hereinabove. The other components of the ninth dose counter 918 beneath the actuator member 920 are essentially the same as those shown in FIGS. 1 and 2 and are not illustrated. As described hereinabove, the actuator member 920 serves as a pivotally mounted lever, the through-hole 922 defining the pivotal mounting. The upwardly-extending protrusion 924 at the intermediate portion of the actuator member 920 defines an input portion of the lever for engagement by the medicament canister 6. The downwardly extending protrusion 926 at the second end of the member 920 carries the driver and defines an output portion of the lever 320b.

In FIG. 30a the dose counter 918 is shown in its neutral arrangement, that is to say the arrangement prior to depression of the medicament canister to dispense a dose of medicament. In this arrangement, the actuator member 920 is biased towards the medicament canister 6 by the compressions spring 930.

The metered-dose inhaler is actuated by the user applying a manual compressive force to the closed end of the medicament canister 6. In response to this compressive force, the canister moves axially with respect to its valve stem (not shown) by an amount varying between 2 and 4 mm. The downwards movement of the canister causes the ferrule to engage with and displace downwards the input portion of the lever (defined by protrusion 924), thereby causing the lever to rotate clockwise about the pivotal mounting (defined by through-hole 922). The output portion of the lever (defined by protrusion 926) includes a driver which directly engages a tooth of the ratchet-tooth wheel 30 to increment the dose counter 318, as described hereinabove with reference to FIGS. 1 and 2. The ninth dose counter 918 may be provided with a control surface to regulate the positions of engagement and disengagement by the driver, as described hereinabove with reference to FIG. 3.

The input portion of the lever (defined by protrusion 924) is positioned between the pivotal mounting (defined by through-hole 922) and the output portion of the lever (defined by protrusion 926), and is relatively closer to the pivotal mounting. As such, the lever serves to amplify a linear input stroke at the input portion so that the output portion provides an increased stroke for indexing the ratchet-toothed wheel 30. This reduces the risk of miscounting, particularly undercounting, and, in turn, reduces the failure rate of the dose counter.

Figure 31:
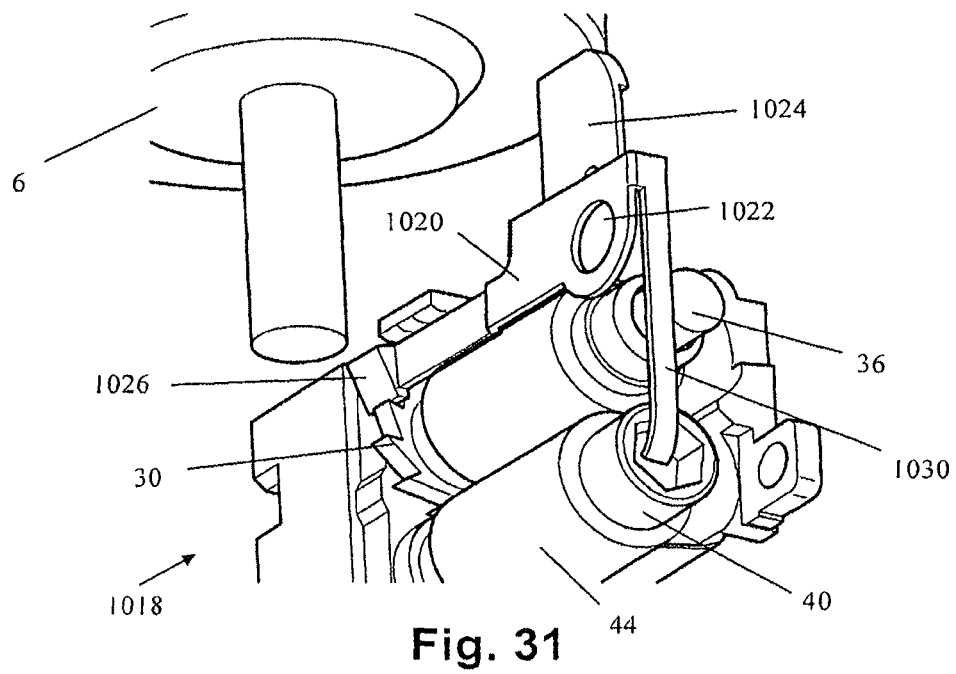
FIG. 31 is a perspective view of part of a tenth dose counter according to the present invention.

FIG. 31 shows an alternative actuator member design for use in a tenth dose counter 1018 according to the present invention. The modified actuator member 1020 differs from the actuator member shown in FIGS. 29 to 30b in that, instead of being formed as a moulded plastics component, it is formed as a stamped metal component. Furthermore, the compression spring for biasing the actuator member towards the medicament canister 6 is replaced by a spring arm 1030. The spring arm 1030 is integrally formed with the actuator member 1020. A distal end of the spring arm 1030 bears against an internal side surface of the inhaler hosing 2 to thereby bias the actuator member towards the medicament canister 6.

Figure 32A:
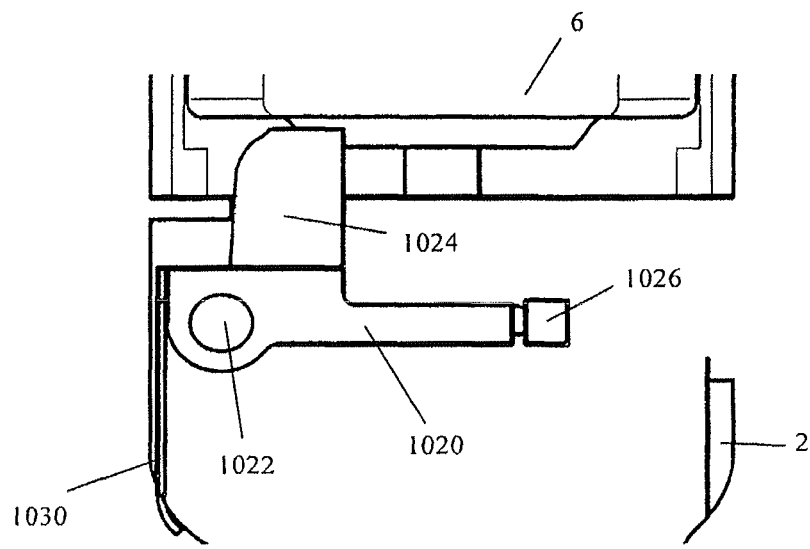
FIGS. 32a and 32b are schematic sectional views of the tenth dose counter for use in explaining its operation.
Figure 32B:
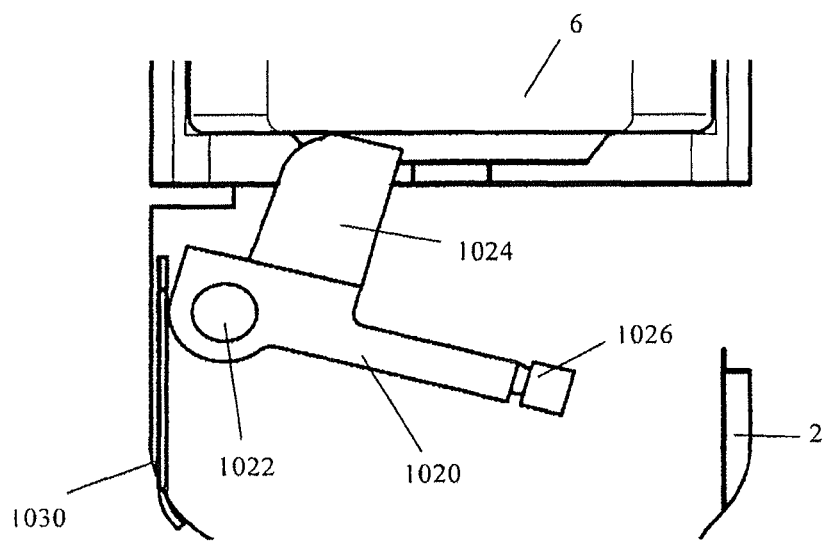

Use of the tenth dose counter 1018 is illustrated in FIGS. 32a and 32b, which are schematic section views showing the tenth dose counter at different stages of actuation.

Figure 33:
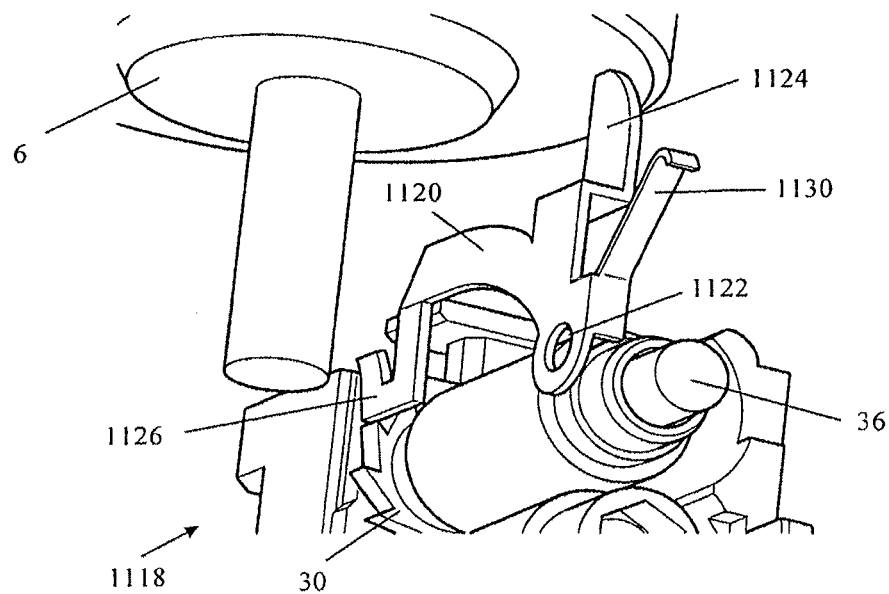
FIG. 33 is a perspective view of part of an eleventh dose counter according to the present invention.

FIG. 33 shows another alternative actuator member design for use in an eleventh dose counter 1118 according to the present invention. The modified actuator member 1120 differs from the tenth actuator member shown in FIGS. 31 to 32b in that it has a different shape, with the spring arm 1130 extending in a different direction. An end of the spring arm 1130 of the actuator member 1120 bears against an internal transverse surface of the inhaler housing 2.

Figure 34A:
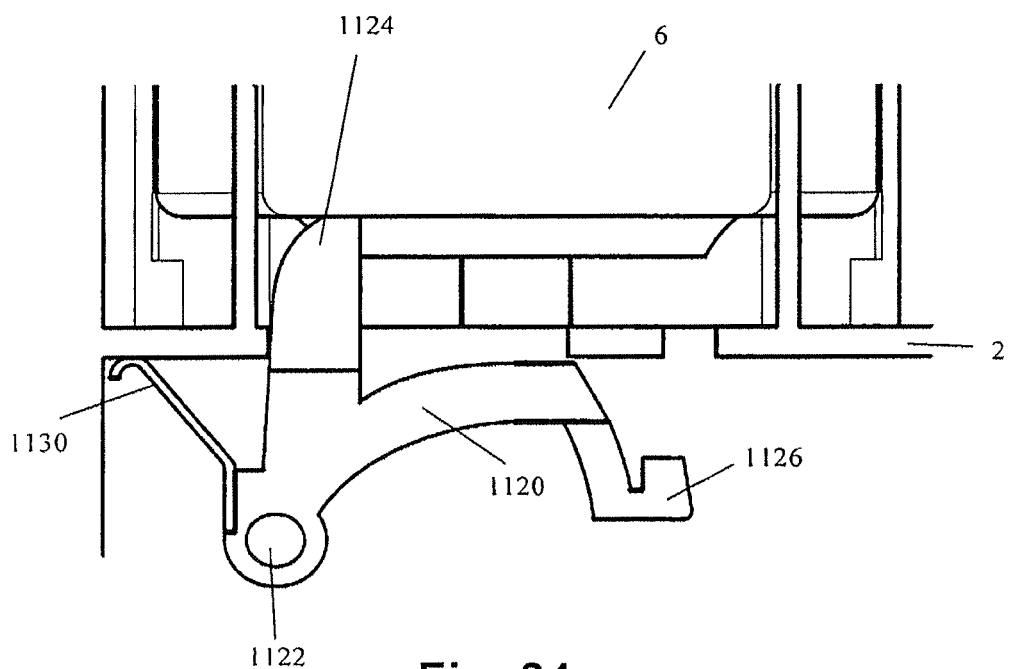
FIGS. 34a and 34b are schematic sectional views of the eleventh dose counter for use in explaining its operation.
Figure 34B:
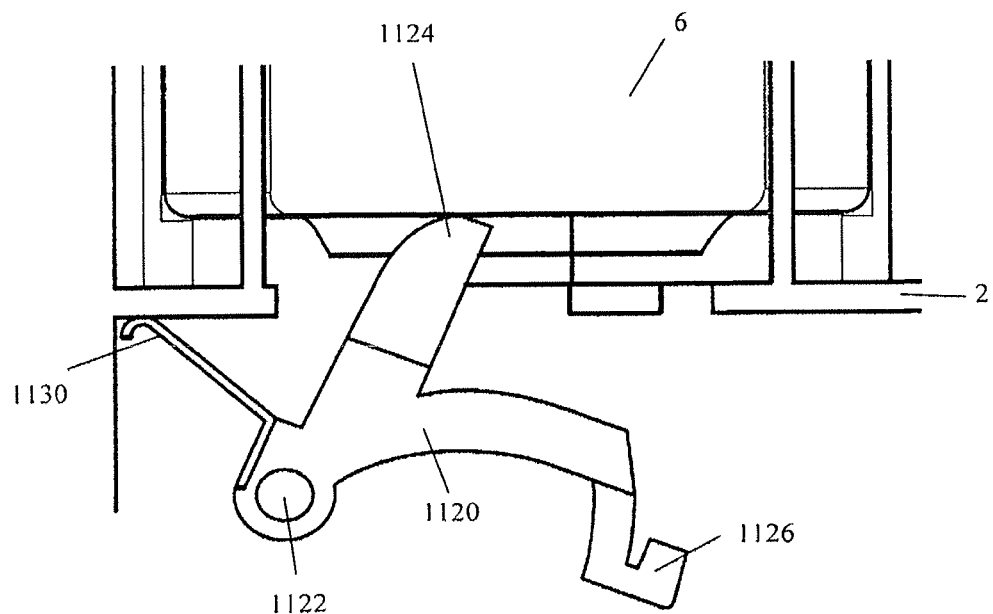

Use of the eleventh dose counter 1118 is illustrated in FIGS. 34a and 34b, which are schematic section views showing the eleventh dose counter at different stages of actuation.

A twelfth dose counter according to the present invention will now be described with reference to FIGS. 35 to 36c. The twelfth dose counter 1218 is similar to the dose counter 18 shown in FIGS. 1 and 2. Thus, the twelfth dose counter 918 includes most of the components of the dose counter shown in FIGS. 1 and 2, including the ratchet-toothed wheel 30, the spindles 36, 40 and the flexible tape 44. A detailed description of these components of the twelfth dose counter 1218 will therefore be omitted, except to the extent that their form or function differs from that described hereinabove. The twelfth dose counter 1218 differs from the counter shown in FIGS. 1 and 2 in that it additionally comprises a pivotally mounted actuator member 1220 carrying a driver 1222 for directly engaging the ratchet-toothed wheel 30. The actuator shaft 20 of the twelfth dose counter 1218 is modified to include an engagement surface 1240 for engaging an input portion 1224 of the actuator member 1220.

Figure 35:
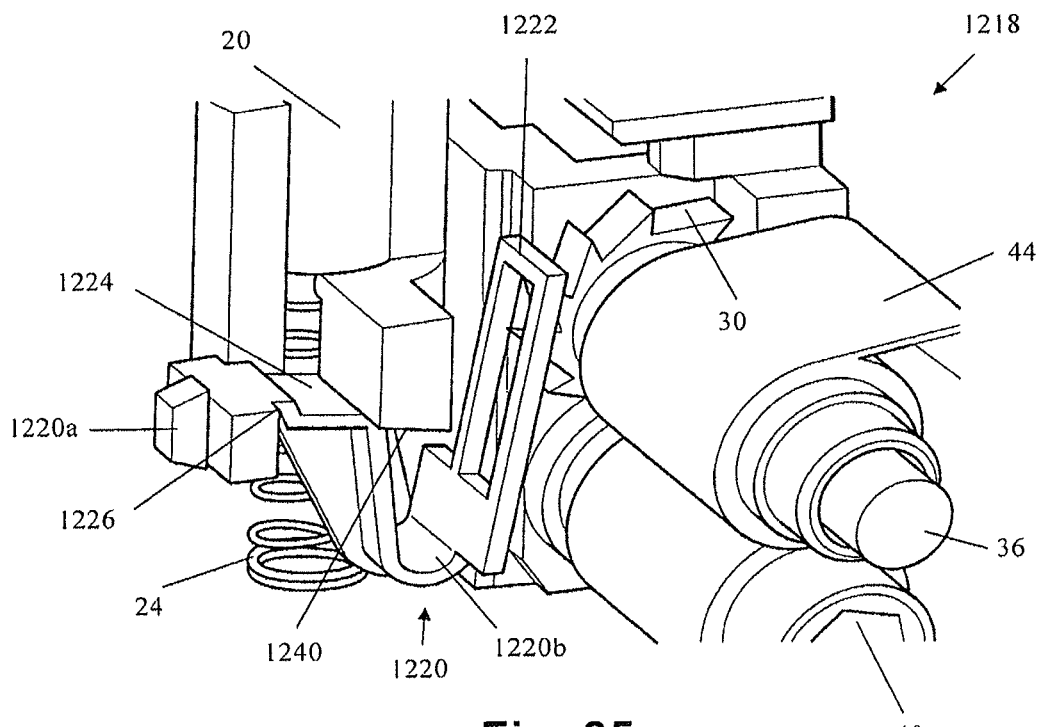
FIG. 35 is a perspective view of part of a twelfth dose counter according to the present invention.
Figure 36A:
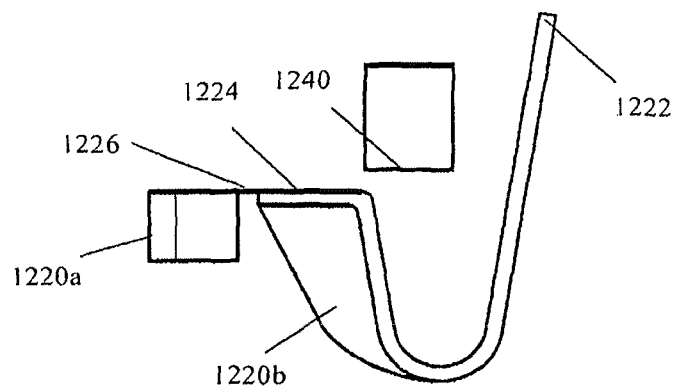
FIGS. 36a to 36c are schematic sectional views of the twelfth dose counter for use in explaining its operation.
Figure 36B:
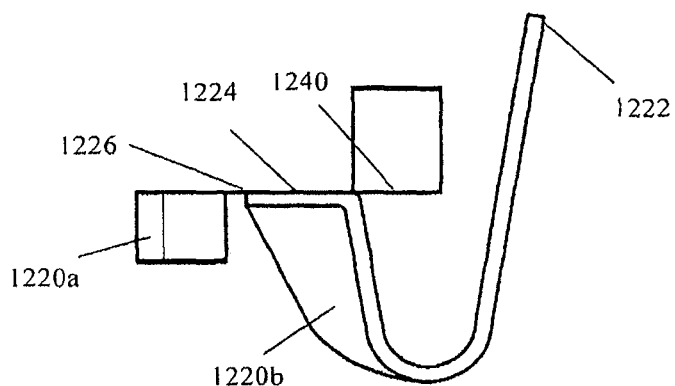
Figure 36C:
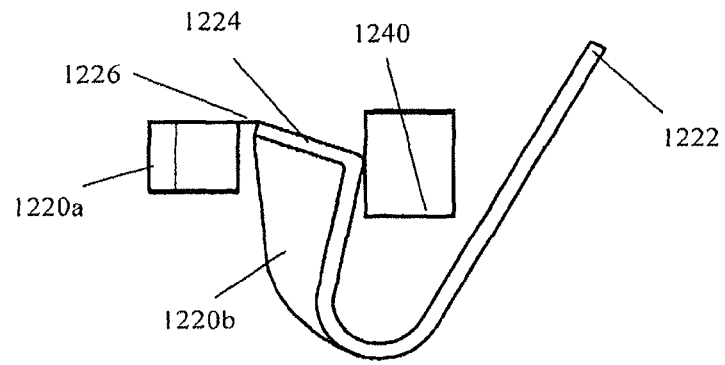

The actuator member 1220 is shown in FIG. 35, which is a perspective view showing certain elements of the twelfth dose counter 1218, and in FIGS. 36a to 36c, which are schematic sectional views showing the twelfth dose counter 1218 at different stages of actuation.

The actuator member 1220 is a moulded plastics component and comprises an integrally formed mounting structure 1220a and lever 1220b. The mounting structure 1220a and lever 1220b are joined together by a living hinge 1226 which defines a pivotal mounting of the lever 1220b. The mounting structure 1220a is fixedly attached to the dose counter chassis (not shown).

The lever 1220b is substantially "U" shaped. A proximal end of the lever 1220b, adjacent to the living hinge 1226, is provided with an upwardly-facing flat engagement surface 1224 which extends in a substantially horizontal plane. A distal end of the lever 1220b carries the driver 1222. The driver 1222 comprises a transversely extending ratchet drive pawl arranged for engaging the teeth of the ratchet-toothed wheel 30. The ratchet drive pawl extends between a pair of spaced apart support arms.

The actuator shaft 20 of the twelfth dose counter 1220 has an upper surface (not shown) arranged for direct engagement by the ferrule of the medicament canister. The actuator shaft is provided with a transverse protrusion which defines a downwardly-facing engagement surface 1240. The actuator shaft 20 is arranged for linear reciprocating movement in a direction parallel to the axis of the medicament canister. The actuator shaft 20 is biased towards the medicament canister by a compression spring 24, as described hereinabove with reference to FIGS. 1 and 2. The engagement surface 1240 of the actuator shaft 20 is arranged to engage the input portion 1224 of the lever 1220b when the actuator shaft is displaced downwards.

Use of the twelfth dose counter 1218 for counting doses dispensed from a metered-dose inhaler will now be described with reference to FIGS. 35a to 36c, which are schematic sectional views showing the dose counter at different stages of actuation. The Figures show the actuator member 1220 of the dose counter 1218 and the engagement surface 1240 of the actuator shaft 20. The other components of the twelfth dose counter 1218 are essentially the same as those shown in FIGS. 1 and 2 and are not illustrated. As described hereinabove, the actuator member 1220 includes a pivotally mounted lever 1220b, the living hinge 1226 defining the pivotal mounting. The input portion of the lever 1224 is arranged adjacent to the living hinge 1226 for engagement by the engagement surface 1240 of the actuator shaft 20. The driver 1222 arranged at the distal end of the lever 1220b defines an output portion of the lever 1220b.

In FIG. 36a the dose counter 1218 is shown in its neutral arrangement, that is to say the arrangement prior to depression of the medicament canister (not shown) to dispense a dose of medicament. In this arrangement, the actuator shaft 20 is biased towards the medicament canister 6 by the compressions spring 24.

The metered-dose inhaler is actuated by the user applying a manual compressive force to the closed end of the medicament canister (not shown). In response to this compressive force, the canister moves axially with respect to its valve stem (not shown) by an amount varying between 2 and 4 mm. The downwards movement of the canister causes the ferrule to engage with and displace downwards the actuator shaft 20, as shown in FIG. 36b. The engagement surface 1240 of the actuator shaft 20 engages the input portion 1224 of the lever 1220b, thereby causing the lever 1220b to rotate clockwise about the pivotal mounting (defined by living hinge 1226). The output portion of the lever (defined by driver 1222) directly engages a tooth of the ratchet-tooth wheel 30 to increment the dose counter 318, as described hereinabove with reference to FIGS. 1 and 2. The twelfth dose counter 1218 may be provided with a control surface to regulate the positions of engagement and disengagement by the driver 1222, as described hereinabove with reference to FIG. 3.

The input portion of the lever 1220b is positioned between the pivotal mounting (defined by living hinge 1226) and the output portion of the lever (defined by driver 1222), and is relatively closer to the pivotal mounting. As such, the lever 1220b serves to amplify a linear input stroke at the input portion of the lever 1220b so that the output portion provides an increased stroke for indexing the ratchet-toothed wheel 30. This reduces the risk of miscounting, particularly undercounting, and, in turn, reduces the failure rate of the dose counter.

FIG. 36c shows the arrangement of the twelfth dose counter 1218 after the driver 1222 has reached the end of its downwards travel, and following further downwards displacement of the medicament canister (not shown). In this arrangement, the engagement surface 1240 of the actuator shaft 20 has become misaligned with the input portion 1224 of the lever 1220b. The engagement surface 1224 of the actuator shaft therefore slips off the edge of the input portion 1224 of the lever 1220b and may continue to move downwards to thereby accommodate overtravel of the canister. As shown in the Figure, the actuator shaft 20 continues to move downwards without causing any further rotation of the lever 1220b.

Figure 37:
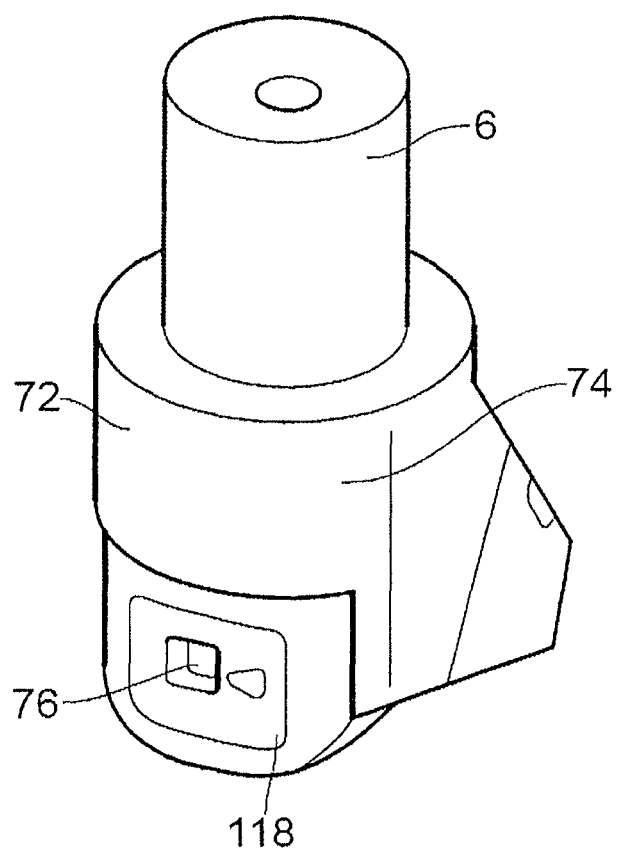
FIG. 37 is a view of a metered-dose inhaler according to the invention.

The present invention further provides a metered-dose inhaler 72 as shown in FIG. 37. The inhaler comprises a medicament canister 6, an actuator body 74 for receiving the canister 6 and having a medicament delivery outlet, and the dose counter as described hereinabove. The actuator body 74 has a window 76 for viewing the display. In a preferred embodiment the actuator body 74 comprises a sump, and preferably a smooth rounded sump. The rounded sump may have a substantially cylindrical upper portion and a substantially hemi-spherical lower portion. By providing a smooth sump the internal surfaces are sufficiently free of protrusions so that during normal use medicament will not substantially adhere thereto.

The medicament canister 6 may contain a medicament in the form of an aerosol. The medicament may be any medicament that is suitable to be delivered to a patient via a metered-dose inhaler. In particular medicaments for the treatment of a wide variety of respiratory disorders are delivered in this manner including anti-allergic agents (e.g. cromoglycate, ketotifen and nedocromil), anti-inflammatory steroids (e.g. beclomethasone dipropionate, fluticasone, budesonide, flunisolide, ciclesonide, triamcinolone acetonide and mometasone furoate); bronchodilators such as: [beta]2-agonists (e.g. fenoterol, formoterol, pirbuterol, reproterol, salbutamol, salmeterol and terbutaline), non-selective [beta]-stimulants (e.g. isoprenaline), and xanthine bronchodilators (e.g. theophylline, aminophylline and choline theophyllinate); and anticholinergic agents (e.g. ipratropium bromide, oxitropium bromide and tiotropium).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, the dose counters described hereinabove are configured to actuate the dose counter on the forward (downwards) stroke of a medicament canister. The dose counters may alternatively be configured to actuate the dose counter of the reverse (upwards) stroke.

The actuator mechanisms of the dose counters described hereinabove comprise levers. Instead of a lever, more complicated linkages may be used to amplify the linear input stroke. Suitable linkages will be apparent to those skilled in the art.

The invention claimed is:

1. A dose counter for counting doses of medicament dispensed by or remaining in a metered-dose inhaler, the dose counter comprising:
   a rotatably mounted gear wheel having a circular arrangement of ratchet teeth;
   a display coupled to the gear wheel, the display having a visible array of dose counting indicia indexable in response to rotary motion of the gear wheel; and
   an actuator mechanism having a driver for rotatably driving the gear wheel in response to the dispensation of a medicament dose, the driver being arranged to engage the ratchet teeth of the gear wheel, wherein the actuator mechanism comprises a pivotally mounted lever having an input portion, the lever being arranged to amplify a linear stroke at the input portion such that a linear stroke of the driver exceeds the linear input stroke,
   wherein the input portion of the lever is arranged between the pivotal mounting and an output portion of the lever,
   wherein the actuator mechanism further comprises a driver shaft mounted for reciprocating movement and carrying the driver, the output portion of the lever being arranged to engage an input portion of the driver shaft.

2. A dose counter as claimed in claim 1, wherein the input portion of the lever is defined by a projection extending from the lever in a direction substantially perpendicular to an imaginary line joining the pivotal mounting and the output portion.

3. A dose counter as claimed in claim 1, wherein the output portion of the lever carries the driver.

4. A dose counter as claimed in claim 3, wherein the lever is resiliently biased towards a starting position, the lever being displaceable against the resilient bias in response to the linear input stroke.

5. A dose counter as claimed in claim 4, wherein the resilient bias is provided by at least one of: a leaf spring separate from the lever, a leaf spring integrally formed with the lever, a compression spring and/or a torsion spring.

6. A dose counter as claimed in claim 1, wherein the driver shaft is resiliently biased towards a starting position, the driver shaft being displaceable against the resilient bias in response to engagement by the output portion of the lever.

7. A dose counter as claimed in claim 6, wherein the resilient bias is provided by a compression spring.

8. A dose counter as claimed in claim 1, wherein the lever is rotatably mounted to a separate mounting structure to thereby provide the pivotal mounting of the lever.

9. A dose counter as claimed in claim 8, wherein the lever is arranged such that a direction of movement of the output portion is substantially perpendicular to a direction of movement of the input portion.

10. A dose counter as claimed in claim 8, wherein the lever is arranged such that a direction of movement of the output portion is substantially parallel to a direction of movement of the input portion.

11. A dose counter as claimed in claim 1, wherein the lever is provided with a flexure hinge arranged between the pivotal mounting and the output portion, the flexure hinge comprising a portion of the lever having reduced flexural strength, and wherein, in use of the dose counter, the flexure hinge is elastically deformable to allow the input portion of the lever to continue to move after the output portion has reached the end of its travel.

12. A dose counter as claimed in claim 1, wherein the pivotal mounting is displaceable against a resilient bias to allow the input portion of the lever to continue to move after the output portion has reached the end of its travel.

13. A dose counter as claimed in claim 1, wherein the lever is provided with a through-hole extending in a direction perpendicular to the pivotal axis, and wherein a mounting post extends through the through-hole with a clearance fit to thereby provide the pivotal mounting.

14. A dose counter as claimed in claim 13, wherein the mounting post carries a preloaded compression coil spring which bears against the lever, the lever being displaceable against the spring preload to allow the input portion of the lever to continue to move after the output portion has reached the end of its travel.

15. A dose counter as claimed in claim 14, wherein the spring preload exceeds the force required at the input portion of the lever to actuate the dose counter, so that the pivotal mounting is not displaced until after the dose counter has been actuated.

16. A dose counter as claimed in claim 1, wherein the lever is arranged such that the linear stroke of the driver is at least 1.1 times a linear output stroke.

17. A dose counter as claimed in claim 1, further comprising means to prevent reverse rotation of the gear wheel.

18. A dose counter as claimed in claim 17, wherein the means to prevent reverse rotation comprises at least one pawl arranged to engage the ratchet teeth of the gear wheel.

19. A dose counter as claimed in claim 1, further comprising a control surface to regulate the position of engagement and disengagement between the driver and the gear wheel.

20. A dose counter as claimed in claim 1, wherein the actuator mechanism is operable by a linear engagement means comprising a medicament canister mounted for reciprocating movement.

21. A dose counter according to claim 1, wherein the driver comprises a ratchet drive pawl.

22. A dose counter according to claim 21, wherein the ratchet drive pawl is arranged between a pair of spaced apart support arms.

23. A dose counter according to claim 1, wherein the display comprises a flexible tape arranged between an indexing spool and a stock bobbin.

24. A dose counter according to claim 1, wherein the input portion of the lever is tapered or rounded for reducing sliding contact when it is engaged by a linear engagement means.

25. A metered-dose inhaler comprising a medicament canister, an actuator body for receiving the canister and having a medicament delivery outlet, and the dose counter as claimed in claim 1.

26. A dose counter for counting doses of medicament dispensed by or remaining in a metered-dose inhaler, the dose counter comprising:
   a rotatably mounted gear wheel having a circular arrangement of ratchet teeth;
   a display coupled to the gear wheel, the display having a visible array of dose counting indicia indexable in response to rotary motion of the gear wheel; and
   an actuator mechanism having a driver for rotatably driving the gear wheel in response to the dispensation of a medicament dose, the driver being arranged to engage the ratchet teeth of the gear wheel, wherein the actuator mechanism comprises a pivotally mounted lever having an input portion, the lever being arranged to amplify a linear stroke at the input portion such that a linear stroke of the driver exceeds the linear input stroke,
   wherein the input portion of the lever is arranged between the pivotal mounting and an output portion of the lever, and wherein a mounting end of the lever is provided with a tongue which is narrower than the lever, and the tongue is inserted in an aperture or slot formed in a thin walled mounting structure such that the mounting end of the lever is able to bear against the mounting structure and define a pivot point, to thereby provide the pivotal mounting of the lever.

27. A dose counter for counting doses of medicament dispensed by or remaining in a metered-dose inhaler, the dose counter comprising:
   a rotatably mounted gear wheel having a circular arrangement of ratchet teeth;
   a display coupled to the gear wheel, the display having a visible array of dose counting indicia indexable in response to rotary motion of the gear wheel; and
   an actuator mechanism having a driver for rotatably driving the gear wheel in response to the dispensation of a medicament dose, the driver being arranged to engage the ratchet teeth of the gear wheel, wherein the actuator mechanism comprises a pivotally mounted lever having an input portion, the lever being arranged to amplify a linear stroke at the input portion such that a linear stroke of the driver exceeds the linear input stroke,
   wherein the input portion of the lever is arranged between the pivotal mounting and an output portion of the lever, and wherein the lever is integrally formed with a mounting structure, the pivotal mounting being provided by a flexure hinge between the lever and the mounting structure.

28. A dose counter as claimed in claim 27, wherein the lever is a moulded plastics component and the flexure hinge is a living hinge.

29. A dose counter as claimed in claim 27, wherein the lever is a stamped metal component and the flexure hinge is a first portion of the component having reduced flexural strength, and wherein, in use of the dose counter, deformation at the flexure hinge is substantially elastic.

30. A dose counter as claimed in claim 27, wherein the mounting structure is provided with an aperture or slot for receiving a male locating feature of a housing, the mounting structure defining at least one barb adjacent to the aperture or slot for engagement with the male locating feature.

31. A dose counter for counting doses of medicament dispensed by or remaining in a medicament canister of a metered-dose inhaler, the dose counter comprising:
   a rotatably mounted gear wheel having a circular arrangement of ratchet teeth;
   a display coupled to the gear wheel, the display having a visible array of dose counting indicia indexable in response to rotary motion of the gear wheel; and
   an actuator mechanism having a driver for rotatably driving the gear wheel in response to the dispensation of a medicament dose, the driver being arranged to engage the ratchet teeth of the gear wheel, wherein the actuator mechanism comprises a pivotally mounted lever having an input portion arranged for direct engagement by the medicament canister of the metered dose inhaler, the lever being arranged to amplify a linear stroke of the medicament canister of the metered dose inhaler at the input portion such that a linear stroke of the driver exceeds the linear input stroke, wherein the input portion of the lever is arranged between the pivotal mounting and an output portion of the lever, and wherein, either:
 (i) the lever is provided with a flexure hinge arranged between the pivotal mounting and the output portion, the flexure hinge comprising a portion of the lever having reduced flexural strength, the flexure hinge being elastically deformable to allow the input portion to continue to move after the output portion has reached the end of its travel; or
 (ii) the pivotal mounting is displaceable against a resilient bias to allow the input portion to continue to move after the output portion has reached the end of its travel.

* * * * *